United States Patent [19]

Jepson et al.

[11] Patent Number: 5,965,387
[45] Date of Patent: Oct. 12, 1999

[54] PROMOTER

[75] Inventors: Ian Jepson; Andrew James Greenland, both of Maidenhead; Michael Bevan; Hilary Sheppard, both of Norwich, all of United Kingdom

[73] Assignee: Zeneca Limited, London, United Kingdom

[21] Appl. No.: 08/718,751

[22] Filed: Sep. 23, 1996

[30] Foreign Application Priority Data

Sep. 22, 1995 [GB] United Kingdom .................... 9519404
Sep. 22, 1995 [GB] United Kingdom .................... 9519406

[51] Int. Cl.⁶ .................................................. C12N 15/00
[52] U.S. Cl. ...................... 435/69.1; 435/320.1; 536/24.1
[58] Field of Search ................................ 435/320.1, 69.1; 536/24.1; 800/205

[56] References Cited

U.S. PATENT DOCUMENTS 5,302,523   4/1994   Coffee et al. ........................ 435/172.1
5,589,614  12/1996   Bridges et al. ......................... 800/205

FOREIGN PATENT DOCUMENTS

90/08826   8/1990   WIPO .
93/01294   1/1993   WIPO .

OTHER PUBLICATIONS

Ronald et al. Gene. vol. 90, pp. 145–148, 1990.
Weidenhaupt et al. Gene. vol. 129, pp. 33–40, 1993.
Parry et al. Gene. vol. 150, pp. 105–109, 1994.
Khan et al. Molecular and Cellular Biology. vol. 10(10), pp. 5150–5159, 1990.
Kim et al. Plant Molecular Biology. vol. 24, pp. 105–117, 1994.
Drews, G.N., et al., "Regional and Cell–Specific Gene Expression Patterns during Petal Development," *The Plant Cell*, 4, 1383–1404 (1992).
Fonné–Pfister, R., et al., "Ring–Methyl Hydroxylation of Chlortoluron by an Inducible Cytochrome P450–Dependent Enzyme from Maize," *Phytochemistry*, 29(9), 2793–2796 (1990).
Frame, B.R., et al., "Production of fertile transgenic maize plants by silicon carbide whisker–mediated transformation," *The Plant Journal*, 6(6), 941–948 (1994).
Guerrero, F.D., et al., "Promoter sequences from a maize pollen–specific gene direct tissue–specific transcription in tobacco," *Mol. Gen. Genet.*, 224, 161–168 (1990).
Hammond–Kosack, M.C.U., et al., "A Practical Guide to Ligation–Mediated PCR Footprinting and in–vivo DNA Analysis Using Plant Tissues," *Plant Molecular Biology Reporter*, 11(3), 249–272 (1993).
Hatzios, K.K., "An Overview of the Mechanisms of Action of Herbicide Safeners," *Z. Naturforsch.*, 46(c), 819–827 (1991).
Holdsworth, M.J., et al., "Site–specific binding of a nuclear factor to the carrot extensin gene is influenced by both ethylene and wounding," *Planta*, 179, 17–23, (1989).

Holt, D.C., et al., "Characterization of the safener–induced glutathione S–transferase isoform II from maize," *Planta*, 196, 295–302 (1995).
Horsch, R.B., et al. "A Simple and General Method for Transferring Genes into Plants," *Science*, 227, 1229–1231 (1985).
Irzyk, G.P., et al., "Purification and Characterization of a Glutathione S–Transferase from Benoxacor–Treated Maize (*Zea mays*)," *Plant Physiol.*, 102, 803–810 (1993).
Itzhaki, H., et al., "An ethylene–responsive enhancer element is involved in the senescence–related expression of the carnation glutathione–S–transferase (GST1) gene," *Proc. Natl. Acad. Sci.*, 91, 8925–8929 (1994).
Jefferson, R.A., et al., "The use of the *Escherichia coli* β–glucuronidase gene as a gene fusion marker for studies of gene expression in higher plants," *Biochemical Society Transactions*, 15(1), 17–18.
Jepson, I., et al., "A Rapid Procedure for the Contruction of PCR cDNA Libraries from Small Amounts of Plant Tissue," *Plant Molecular Biology Reporter*, 9(2), 131–138 (1991).
Kuhlemeier, C., et al., "Regulation of Gene Expression in Higher Plants," *Ann. Rev. Plant Physiol.*, 38, 221–257 (1987).
Lamoureux, G.L., et al., "The Role of Glutathione and Glutathione–S–Transferases in Pesticide Metabolism, Selectivity and Mode of Action in Plants and Insects," D. Dolphin, R. Poulson and O. Avramovic (Eds), *Coenzymes and Cofactors*, vol. 3: Glurathione: chemical, biochemical and medical aspects, part B, John Wiley and Sons, New York, pp. 153–196 (1989).
Mannervik, B., et al., "Glutathione Transferases—Structure and Catalytic Activity," *CRC Critical Reviews in Biochemistry*, 23(3), 283–337 (1988).
Mett, V.L., et al., "Copper–controllable gene expression system for whole plants," *Proc. Natl. Acad. Sci.*, 90, 4567–4571 (1993).
Moore, R.E., et al., "Cloning and expression of cDNA encoding a maize glutathione S–transferase in *E. coli*," *Nucleic Acids Research*, 14, 7227–7235 (1986).
Mozer, T. J., et al., "Purification and Characterization of Corn Glutathione S–Transferase," *Biochemistry*, 22, 1068–1072 (1983).
Sanger, F., et al., "DNA sequencing with chain–terminating inhibitors," *Proc. Natl. Acad. Sci.*, 74(12), 5463–5467 (1977).

(List continued on next page.)

*Primary Examiner*—James Ketter
*Assistant Examiner*—Irem Yucel
*Attorney, Agent, or Firm*—Liza D. Hohenschutz

[57] ABSTRACT

A chemically inducible gene promoter sequence, and particularly, but not exclusively, a chemically inducible gene promoter sequence based on cis regulatory elements from the maize glutathione S-transferase 27 (GST-27) gene. In a preferred embodiment, the promoter sequence is operatively linked or fused to a gene or series of genes whereby expression of the gene or series of genes may be controlled by application of an effective exogenous inducer.

25 Claims, 19 Drawing Sheets

OTHER PUBLICATIONS

Schena, M., et al., "A steroid–inducible gene expression system for plant cells," *Genetics*, 88, 10421–10425 (1991).

Timmerman, K.P., "Molecular characterization of corn glutathione S–transferase isozymes involved in herbicide detoxication," *Physiologia Plantarum*, 77, 465–471 (1989).

Watson, J.C., et al., "Purification and Restriction Endonuclease Analysis of Plant Nuclear DNA," *Methods in Enzymology*, 118, 57–75 (1986).

Weinmann, P., et al., "A chimeric transactivator allows tetracycline–responsive gene expression in whole plants," *The Plant Journal*, 5(4), 559–569 (1994).

Wiegand, R.C., et al., "Messenger RNA encoding a glutathione–S–transferase responsible for herbicide tolerance in maize is induced in response to safener treatment," *Plant Molecular Biology*, 7, 235–243 (1986).

Williams, S., et al., "Chemical Regulation of *Bacillus Thuringiensis* ∂–Endotoxin Expression in Transgenic Plants," *Bio/Technology*, 10, 540–543 (1992).

Sambrook, J., et al., *Molecular Cloning–A Laboratory Manual*, 1989, pp. 1.3–1.20.

Fromm, M.E., et al., *Bio/Technology*, "Inheritance and Expression of Chimeric Genes in the Progeny of Transgenic Maize Plants," 8, 833–839 (1990).

Spychalla, J.P., et al., *Plant Tissue Culture Manual*, "Agrobacterium–mediated transformation of potato stem and tuber tissue, regeneration and PCR screening for transformation," B11, 1–18 (1983).

Fig. 1A

```
gaattccaaatatatgatgattgttgtcctagtgcagaagaactaaatatactagcgaaaaaaccttc
ctagtcatgtaagtgtatgggcatatagaaaataaacatctcaagactccaaactagtcatagctttta
gtcacaacttcaaacacttcatgccaacagatcatgattttttttgcctaagacaaaactagaat
gagaaaagaactaactcatcatcatcatagtatgcatcacaaaaatgacacatatgatACTAT
ATCACACAGGCCTTCAGTTTCTAGAACAAGTGCAGATCGAtgtgtgggtatgcatgtctaatatttact
aggttggatatgcatgggcgttcattcagaatcagttcacacagtttatcgcacttctgtttacaaaac
atggattcattgctctgtctggctactgcgtaaggatcaacttgtctaatctaggtgcatcctccctt
gtcaagcaaacttaacaatttgataaaaaatgcagctttatatgtgaacccataactaatatga
caggaaactgatgtgcaacaacaaatactaAAAAACTAAAATAGGAaaacacagttccaaatgtataattg
tcaccatagtagtgcaaaagaaccaaatactgcagagaaaacttcctagtcagtaagtATGGACATAT
AGAAATAAACATCTCAAGACTCCAATAACAGGCTCAAGCTAACTAGTCATGGCTGTTTTTTTCCTAGGAA
GCAAACTAGTCACAACTTTAAACATTTCATGCCAACAAGATCATCAGGATAGTATCGTATAGACACGTATATGATA
AAGCTAGAATGAGAGAAAAGACCTAACTCAGCATACATATCAGGATAGTATCGTATAGACACGTATATGATA
CTATATCACGCCAGCCGTTCAATTTCTAGAACAAATGCAGATTGATCTGTGAATATGCATGTCTCATATTT
TACTAGGTTGGATGGACTGAATCCCGTGAATCCCGTGAAACAAACAATTTATTCAACAAgttctgcatgaatatcatc
tcaaattcaataatcactccgttgataaaaaatgcaaccaacagttaaccagaagtgaaatagaaac
tatttgaatcagatcactcctccgttattcacatacacagtaacaagaacagtagaagcagtaggaac
attgtttacccatcaatttcaagtacaacagtaacaagaacagtagaattgagcatgtgagtATT
GTTGATACCTTCGTTGAGCTCTCTCTGCCGCGGCTTTCTGCGCagcaagagccagctcaggatccacc
ccgaaagcttgggcgtaggtgttgtctatcggcgaaacacgcgcgcggtacgccaagagcgcggccat
```

Fig. 1B

```
ctccatccaggcacggtgcgcccgctttttcgccgtctcgctgagtcacgcgggcgtccagcaggtag
ttgagcgcttccgcggcacgacgaatcgcgtgcgcggcccGGATCTGGTCGAGTTGGTAGTCAGCGTCGGT
GTCGAATGCCCGGACGTCgaccaggaagaagttgccgtcgctggggtgggacggaaggcgtcaggattg
tcgcaagggcagagcccagcCTGCGGcgGGGCTACCTCGTCGACGCCTCCGgCACGCCCGGCAAAGCT
GcTGCGGGAcgTGCcccgCCTGGGCgCCTTCTCGGTGAAGTGGtCCtcgaagggacgagctcgctgggg
tcaaaccaccccatagctcGAGTCACcGAAgAAGGCGACGAGGACGAGCCCGTcgCGGTGGCCgcgGTGT
ACCTCCTCGTCGTCGGTGAggctGAGCGCTGTAGATATGGCCAGGCcACCGGATGGGACTTCACCTTGG
CCCAGACCATGTCGcCGAACCGGGGGCCGCCGTTCGCCCATGCGATgCCGGCAGCAGGAACCAT
GGcGCCTCCAGCGGCGGGGGTCGGACATCCTGTGGAGGGGAAACCGAAAACCTAGATTTGGATGCAGGTTCG
ATTGGTCTCGGCTTGGGTTTGGTTCCGGAGGAGGGTGGCCTGGGATCGGTGGAAGGAGGACATTGTTG
GTAATTTTATTATTTATAATGGAGAAATTCGAGAGACTGAACGATGGTGATGTTTATTTGAGGACT
ATGTAGTATAAAgtgtAAAAATAGTATTTTATCAAGTTTATATTCACGTTTTGCTGAAGATAGTATAATA
GTGGAGTTGTTTTGGCGGCTACATATTTAAATTCACTTTGTTGTAATCTACACTATAAAATAGTGTTTTACACGGTATGTTGT
CACATTCTCTATTTTAAATTCACTTTGTTGTAATCTACACTATAAAATAGTGTTTTACACGGTATGTTGT
ACACAGCCTTATCGTGCGCGAcgGAGTTGGATAGAGATGGTGAACAGCTGGATAGATATGATTTATAGG
CGATTGGGTAGATGTGATTTGATAGGTGGTAGATATGATTTTAATGGAGGCGATTAGTGAGACATTGTAAATAATTAGG
TTGATGTGATCCGAGGATGGCTAGGTAGATGGCTAGATATGATTTTAATGGAGAATGGTTTGGTGGACTAAGTTATGTGGA
CATTATAATATGTTTTAAATTTCTAAGAAATTTGTTGTGTTAAATTGTATCCCACATAGATTATTAGCC
ATCTCAAAGAGAGGTTTGGGTTTGTTTACACAGAATAACAATATTCGTTTGCTTCTACAATTTATATGTTTT
TATTTACATGAAAACTATATTTTTTATTCATTCATTCTACTCACCCCAGCACAGAAATTCTGTTGAGTAGATGAA
```

Fig. 1C

```
AAAAAACTACAACAAACTCTTCCTGAAAGTGTCGGTGTGAAGCCGAGAAATCCTTTCATTTCGGTGACG
GAGCCCCTTGCTGCTGGCTGCTGCTCAGTGCACTCCGTTCCGCCTGCCTGCCACTACAAGCGACGGCCGACGAC
TCGCAAGTATCGGTAGGCATTTAAAACTGAAAACCAAATCTAAACCCGAATAGACCAAATTGTTGGTTT
ATTCGGGTTTTTGGGTTCGGATTCGGTTTCTAAATGCTATATTTTAGGGTATAGGTTCGGGTTCAGTT
TCTAACCTTTAAAAACCTGAATAGACGAATAACCCGAAATATAAAAAATCTCTTAATATGTGATGATATTA
TTATATGATTATGAACTTATTAACCGAAATAATGATACCATCCTAACGATAGTATATATCTATGTA
TGCTATTTTATAGTCACTGTTGTAATAATAGTACTTCCAATTAATCAGTGTATATATTTTAACA
AAAGATACTAGCCTCTCTACTATTTGAGTATATTCGGTGCACCGAATAGACCGAATAGACCGAAATTGTAAGTC
TATTCAGGTTCGGTTCCTAAAATTATTTAAAAATTTTGGTTCTCATATTTCAGAATCCGAAATTTCATA
AATCCAAATAGACCGAACCAAATTaCGCTAATAGACCTAGCGTACTCGCAAGTCGCACCCCAC
TAGCCCTGCTGCGTGCGTAAGCGAGGACGTCACGCGTTCTCCCCACCCAGAACCAGCGCCagCTctAACGTCACCT
TAGCACCTTCTTCCTCTCCTCCTCTATTGCTAGCTGCTGATCTTGATCCTGCACCCGAGCCGTACACAAGAGCTAGTCGGTAG
CTGATTTTCTCTCTCCCATCCAATTCCAGCTGCTGATCTTGATCCTGCACCCCGAGCCGTACACAAGAGCTAGTCGGTAG
CACACCCCATCCAATTCCAGCTGCTGATCTTGATCCTGCACCCCGAGCCGTACACAAGAGCTAGTCGGTAG
AACTTGCAGGAGCGGAgCAGAACTAAGTGCAGAGAACAGGACATATG
```

TSP

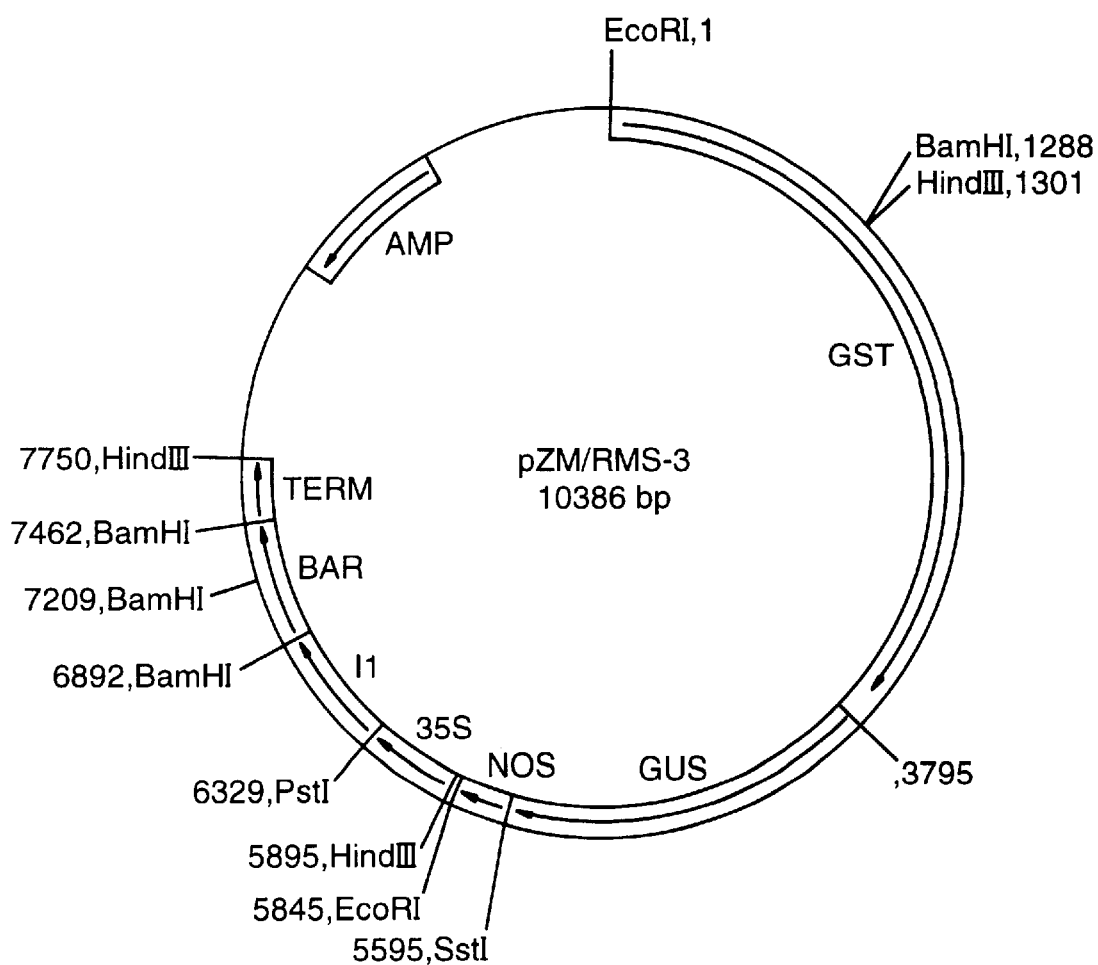

KEY TO GENES
1=nos TERMINATOR
2=BAR GENE
3=Adh 1 INTRON
4=CaMV 35S
5=GST PROMOTER
6=GUS GENE
7=nos TERMINATOR
8=AMPICILLIN RESISTANCE

Fig. 14.

```
5' TCGGTTCCTAAAATTATTTTAAAAATTTGGTTCTCCATATTCAGAATCCGAAATTTCATAAATCC 3'
3' CCAAGGATTT 5'           3' CTTAGGCTTTA 5'           3' TTAAAGTATTT 5'
   Probe 326                  Probe 284                    Probe 275
                                      3' ATAAAGTCTTA 5'
                                         Probe 290

Probe ERE   TATTTCAAAAT
            ATAAAGTTTTA
```

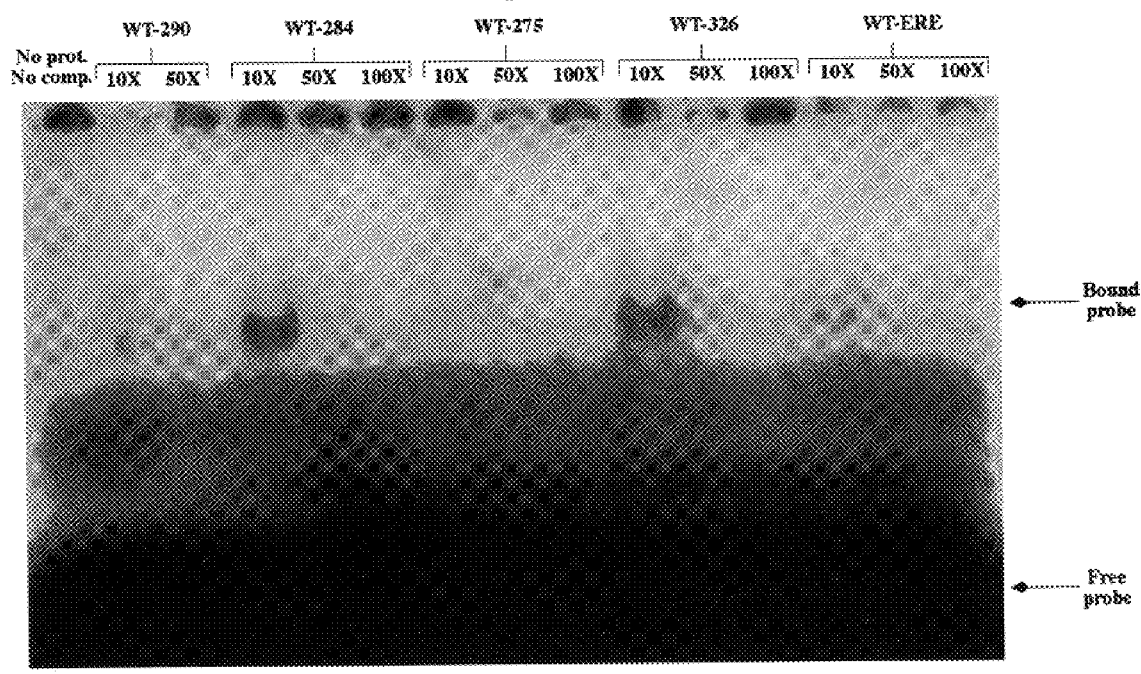

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 3827 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (C) INDIVIDUAL ISOLATE: PROMOTER OF GSTII 27KD SUBUNIT (xi) SEQUENCE DESCRIPTION: SEQ ID NO:1:

```
GAATTCCAAA TATATGATGA TTGTTGTCCT AGTGCAGAAG AACTAAATAT ACTAGCGAAA        60

AAAAACCTTC CTAGTCATGT AAGTGTATGG GCATATAGAA AAATAAACAT CTCAAGACTC       120

CAAACTAGTC ATAGCTTTTA GTCACAACTT CAAACACTTC ATGCCAACAA GATCATGGAT       180

TTTTTTTTTT GCCTAAGACA AAACTAGAAT GAGAAAAGAA CTAACTCATC ATACATATTA       240

GTATGGCATC ACAAAAAAAA TGACACATAT ATGATACTAT ATCACACAGG CCTTCAGTTT       300

CTAGAACAAG TGCAGATCGA TGTGTGGGTA TGCATGTCTA ATATTTTACT AGGTTGGATA       360

TGCATGGGCG TTCATTCAGA ATCAGTTTCA CACAGTTTAT CGCACTTCTG TTTACAAAAC       420

ATGGATTTCA TTGCTCTGTA CTGGCTACAT GCGTAAGGAT CAACTTGTCT AATCTAGGTG       480

CATCCTCCTT GTCAAGCAAA CTTAACAATT TGATAAAAAA AAATGCAGCT TTTATATGTG       540

AACCCATAAC TTAATATGGA CAGGAAACTG ATGTGCAACA ACAAAAACTA AAATAGGAAG       600

GAAACACAAG TTCCAAATGT ATAATAATTG TCACCATAGT GCAAAGAAC CAAATATACT        660

GCAGAGAAAA CTTCCTAGTC ATGTAAGTGT ATGGACATAT AGAAATAAAA CATCTCAAGA       720

CTCCAATAAC AGGCTCAAGC TAACTAGTCA TGGCTTTAAA CCTTCATGAT GCAAACTAGT       780

CACAACTTTA AACATTTCAT GCCAACAAGA TCATGGATGG TGTTTTTTTT TCCTAGGGAA       840

AAGCTAGAAT GAGAAAAGAC CTAACTCAGC ATACATATCA GGATAGTATC GTATAGACAC       900

GTATATGATA CTATATCACG CAGCCGTTCA ATTTCTAGAA CAAATGCAGA TTGATCTGTG       960

AATATGCATG TCTCATATTT TACTAGGTTG GATGGACTGA ATCCCGTGAA ACAAACAATT      1020

TATTCAACAA GTTTCTGCAT GAATATCATC TCAAATTCAA TAATCACTCT CGTTGATAAA      1080

AAAAATGCAA CCAACAGTTA ACCAGAAGTG AAATAGAAAC TATTTGAATC AGATCACTCC      1140

GTTATTCACA TCAAAATAAT TGTTGCTTGA TCTATAAAAG CAGTAGGAAC ATTGTTTACC      1200

CATCAATTTC AAGTACACAG TAACAAGAAC AGTACAGCTA GAATTGAGCA TGTGAGTATT      1260

GTTGATACCT CGTTGAGCTC TCTCTGCCGC GGCTTTCTGC TCGGCAGCAA GAGCCAGCTC      1320

AGGATCCACC CCGAAAGCTT GGGCGTAGGT GTTGTCTATC GGCGAAAACA CGCGCGGTAC      1380

GCCAAGAACA GCGCGGCCAT CTCCATCCCA GGCACGGTGC GCCCGCTTTT TCGCCGTCTC      1440

GCTGAGTCAC GGCGGGCGTC CAGCAGGTAG TTGAGCGCCT TCCGCGGCAC GAATCGCTGC      1500

GTGCGGCCCG GATCTGGTCG AGTTGGTAGT CAGCGTCGGT GTCGAATGCC GGGACGTCGA      1560

CCAGGAAGAA GTTGCCGTCG CTGGGGTGGG GACGGAAGGC GTCAGGATTG TCGCAAGGGC      1620

AGAGCCCAGC CTGCGGGCGG GGCTACCTCG TCGACGCCTC GGCACGGCGG CGGCAAAGCT      1680

GCTGCGGGAC GTGCCCGCCT GGGCCGCCTT CTCGGTGAAG TGGTCCTCGA AGGGGACGAG      1740
```

-continued

```
CTCGCTGGGG TCAAACCACC CCATAGCTCG AGTCACCGAA GAAGGCGACG AGGACGAGCC    1800

CGTCGCGGTG GCCGCGGTGT ACCTCCTCGT CGTCGGTGAG GCTGACGCTG TAGATATGGC    1860

CAGGCCACCA CGGATGGGAC TTCACCTTGG CCCAGACCAT GTCGCCGAAC CGGGGGCCGC    1920

CGTTCGCCCA TGCGATGCCG CGTCCGGCAG CAGGAACCAT GGCGCCTCCA GCGGCGGGGT    1980

CGGACATCCT GTGGAGGGGA ACCGAAAACC TAGATTTGGA TGCAGGTTCG ATTGGTCTGG    2040

GCTTGGGTTT GGGTTCCGGA GGAGGGTGGC CTGGGATCGG TGGAAGGAGG GACATTGTTG    2100

GTAATTTTTA TTATTTTATA ATATGGAGAA ATTCGAGAGA CTGAACGATG GTGATGTTTA    2160

TTTGAGGACT ATGTAGTATA AAGTGTAAAA TAGTATTTTA TCAAGTTTAT ATTCACGTTT    2220

TTGCTGAAGA TAGTATAATA GTGGAGTTGT TTTTGGCGGC TACATAATCT TAGGCTATCT    2280

TCTCGGTCGC TCTCATATCA TATCTACTAT CACATTCTCT ATTTTAAATT TCACTTTGTG    2340

TAATCTACAC TATAAAATAG TGTTTTACAC GGTATGTTGT ACACAGCCTT ATCGTGGCGC    2400

GACGGAGTTG GATAGAGATG GTGAACAGCT GGATAGATAT GATTTATAGG CGATTGGGTA    2460

GATGTGATTT GATAGGTGGT TATGTAGGAG CGATTAGTG AGACATTGTA AATAATTAGG     2520

TTGATGTGAT CCGAGGATGG CTAGGTAGAT ATGATTTTAA TGGATGGTTT GGTGGACTAA    2580

GTTATGTGGA CATTATAATA TGTTTTAAAT TTCTAAGAAA TTGTTTGTGT TAAATTGTAT    2640

CCCACATAGA TTATTTAGCC ATCTCAAAGA GAGGTTTGGG TTGTTTACAC AAATAAAATA    2700

TTCGTTTGCT TCTACAATTT ATATGTTTTT TATTTACATG AAAACTATAT TTTTTATTCA    2760

TCTACTCACC CAGCACAGAA ATTCTGGTTG AGTAGATGAA AAAAAACTAC AACAAACTCT    2820

TCCTGAAAGT GTCGGTGTGA AGCCGAGAAA TCCTTTTCAT TTCGGTGACG GAGCCCCTTG    2880

CTGGCTGCTG CTCAGTGCAC TCCGTTCGCC TGCCTGCCAC TACAAGCGAC GGCCGACGAC    2940

TCGCAAGTAT CGGTAGGCAT TTTAAAACTG AAAACCAAAT CTAAACCCGA ATAGACCAAA    3000

TTGTTGGTTT ATTCGGGTTT TTGGGTTCGG ATTCGGTTTC TAAATATGCT ATATTTTAGG    3060

GTATAGGTTC GGGTTCAGTT TCTAACCTTT AAAACCTGAA TAGACGAATA ACCCGAAATA    3120

TAAAAAATCT CTTAATATGT GATGATATTA TTATATGATT TATGAACTTA TTAACCGAAA    3180

ATAATGATAC CATCCTAACG ATAGTATATA TATCTATGTA TGCTATTTTT ATAGTCACTT    3240

GTTGTAATAA TAGTACTTCC AATTAATTAA TCAGTGTATA TATTTAACA AAAGATACTA     3300

GCCTCTCTAC TATTTGAGTA TATTCGGTGC ACCGAATAGA CCGAACCGAA ATTGTAAGTC    3360

TATTCAGGTT CGGTTCCTAA AATTATTTTA AAAATTTTGG TTCTCATATT TCAGAATCCG    3420

AAATTTCATA AATCCAAATA GACCGAACCA AATTACGCTA ATAGACCGAA TAACTAGCGT    3480

ACTCGCAAGT CGCACCCCAC TAGCCTGCTG CGTGCGTAAG CGAGGACGTC ACGCGTTCTC    3540

CCTCCCGTCG ACCAAATACA CTTGGTCTTC TAGCACCTTC TTCCTCTCCA AGACTCCAAT    3600

CCCCCAACCA CCAGAACCAG CGCCAGCTCT AACGTCACCT CTGATTTCTC TCTCCTCTCT    3660

ATTGCTAGCT GCTTTATTAT AAGTAGCAGC TGCAGCAGGC AGGAGCTGCA CACACCCATC    3720

CAATTCCAGC TGCTGATCTT GATCCTGCAC CCCGAGCCGT ACACAAGAGC TAGTCGGTAG    3780

AACTTGCAGG AGCGGAGCAG AACTAAGTGC AGAGAACAGG ACATATG                  3827
```

(2) INFORMATION FOR SEQ ID NO:2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
 (C) INDIVIDUAL ISOLATE: MAIZE GSTII 27 FOOTPRINT SEQUENCES (xi) SEQUENCE DESCRIPTION: SEQ ID NO:2:

CCAAGAGTAT AAAGTCTTAG GCTTTAAAGT ATTTAG                                    36

(2) INFORMATION FOR SEQ ID NO:3:

(i) SEQUENCE CHARACTERISTICS:
  (A) LENGTH: 63 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (C) INDIVIDUAL ISOLATE: RETARD PROBE FOR G290 FOOTPRINT (xi) SEQUENCE DESCRIPTION: SEQ ID NO:3:

GGATTTTAAT AAAATTTTTA AAACCAAGAG TATAAAGTCT TAGGCTTTAA AGTATTTAGG           60

TTT                                                                        63

(2) INFORMATION FOR SEQ ID NO:4:

(i) SEQUENCE CHARACTERISTICS:
  (A) LENGTH: 66 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (C) INDIVIDUAL ISOLATE: FIGURE 14 SEQUENCE (xi) SEQUENCE DESCRIPTION: SEQ ID NO:4:

TCGGTTCCTA AAATTATTTT AAAAATTTTG GTTCTCATAT TTCAGAATCC GAAATTTCAT           60

AAATCC                                                                     66

(2) INFORMATION FOR SEQ ID NO:5:

(i) SEQUENCE CHARACTERISTICS:
  (A) LENGTH: 11 base pairs
  (B) TYPE: nucleic acid
  (C) STRANDEDNESS: single
  (D) TOPOLOGY: linear (ii) MOLECULE TYPE: DNA (genomic)

(vii) IMMEDIATE SOURCE:
  (B) CLONE: FIGURE 14 SEQUENCE 2

(xi) SEQUENCE DESCRIPTION: SEQ ID NO:5:

CTTAGGCTTT A                                                               11

(2) INFORMATION FOR SEQ ID NO:6:

(i) SEQUENCE CHARACTERISTICS:
  (A) LENGTH: 11 base pairs
  (B) TYPE: nucleic acid
  (C) STRANDEDNESS: single
  (D) TOPOLOGY: linear (ii) MOLECULE TYPE: DNA (genomic)

(vii) IMMEDIATE SOURCE:
  (B) CLONE: FIGURE 14 SEQUENCE 3

(xi) SEQUENCE DESCRIPTION: SEQ ID NO:6:

CCAAGGATTT T                                                                                           11

(2) INFORMATION FOR SEQ ID NO:7:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: FIGURE 14 SEQUENCE 4

(xi) SEQUENCE DESCRIPTION: SEQ ID NO:7:

ATAAAGTCTT A                                                                                           11

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: FIGURE 14 SEQUENCE 5

(xi) SEQUENCE DESCRIPTION: SEQ ID NO:8:

TTAAAGTATT T                                                                                           11

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: FIGURE 14 SEQUENCE 6

(xi) SEQUENCE DESCRIPTION: SEQ ID NO:9:

TATTTCAAAA T                                                                                           11

(2) INFORMATION FOR SEQ ID NO:10:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: FIGURE 14 SEQUENCE 7

(xi) SEQUENCE DESCRIPTION: SEQ ID NO:10:

ATAAAGTTTT A                                                                                           11

PROMOTER

BACKGROUND OF THE INVENTION

The present invention relates to a promoter and to a construct comprising the same.

In particular, the present invention relates to a chemically inducible gene promoter sequence, and particularly, but not exclusively, a chemically inducible gene promoter sequence based on cis regulatory elements from the maize glutathione S-transferase 27 (GST-27) gene. The present invention also relates to gene constructs, expression systems, plants and promoter/inducer combinations comprising the chemically inducible gene promoter sequence.

Recent advances in molecular biology techniques have resulted in a better understanding of plant promoters. Cis-regulatory elements have been identified and used to localise reporter gene activity to specific differentiated cell types and to defined stages of plant development (Drews et al., 1992; Guerrero et al., 1990). While current technology exists to regulate trans-gene activity in a spatial or temporal manner, the external control of introduced genes by application of an inducing chemical is not well established in plants.

The ability to regulate genes in an inducible manner is well established in bacteria, fungi, insects and animal cell cultures. For inducible regulation systems to be effective there should be a zero or low level of expression in the absence of inducer, high expression following treatment with inducer and no effect of the inducer on other cellular functions.

Whilst numerous inducible genes have been isolated from plants (Kuhlemeier et al., 1987), a well defined inducible regulation system is not in common use. A number of genes have been described which are activated by pathogen attack or environmental stimuli, including light, oxygen and temperature levels. Although some of these are well characterised at the molecular level, they cannot be utilised for inducible genes system due to illegitimate activation by environmental signals.

The involvement of chemical stimuli, including plant growth regulators, in activation of gene transcription is well documented in plants. Application of these compounds may be better controlled, in comparison with environmental stimuli, however they cannot be considered for inducible genes systems due to undesirable pleiotropic effects.

A number of recent studies have demonstrated that control of trans-genes in plants can be achieved by application of exogenous chemicals. These include activation by salicylic acid (Williams et al., 1992), tetracyline (Weinmann et al., 1994], glucocorticoids (Schena et al., 1991) and copper ions (Mett et al., 1993). Although these systems fulfil the prerequisites described earlier, and therefore have utility for research applications, their use will be limited as the chemicals described are not compatible with current agricultural practice.

A potentially attractive group of chemicals which may have utility in regulating gene expression in transgenic plants are herbicide safeners. These compounds are currently used in agriculture and function to selectively elevate the metabolism of certain herbicides, primarily by inducing the detoxifying enzymes, glutathione S-transferase (Hatzios, 1991) and cytochrome p450-dependent mixed function oxidises (Fonne-Pfister and Kreuz, 1990). Glutathione S-transferases (GSTs) are multi-functional enzymes which catalyze the conjugation of the thiol group of glutathione to electrophilic centres of lipophilic compounds leading to their detoxification (Mannervik and Danielson, 1988). GSTs are ubiquitous and their role in xenobiotic metabolism in mammals and plants (Lamoureux and Rusness 1989) is well established.

The best characterised system of plant GSTs is found in maize, where they account for 1–2% of soluble protein (Timmerman, 1989). Four isoforms of GST have been described in maize, GST I (Mozer et al., 1983; Weigand et al., 1986), GST II (Mozer et al., 1983; Holt et al., 1995), GST III (Moore et al., 1986) and GST IV (Irzyk and Feurst, 1993). GST-27 is a component of GST II and GST IV which exhibit safener dependent inducibility.

In our International Patent Publication No. W093/01294, the teaching of which is hereby incorporated by reference, we demonstrated that the promoter region controlling GST-27 can be used to achieve safener dependant trans-gene expression. These studies revealed that a 3.8 kb GST-27 promoter, in addition to directing safener inducible trans-gene expression, also gave a constitutive level of expression in root tissues.

BRIEF SUMMARY OF THE INVENTION

The present invention seeks to provide, by the use of detailed promoter analysis, a deleted GST promoter which still maintains the advantages of chemical inducibility. In this regard, we have, through the use of deletions and mapping of cis-regulatory elements, identified sequences involved in safener responsiveness. The use of these sequences can be used to enhance gene switch performance. For example, once a cis-element involved in inducible expression has been identified, it is possible to enhance inducibility for example by multimerising the element.

There are examples (copper inducible switch, Mett et al, 1993) where inducible promoter systems have been developed for plants where a cis-regulatory element conferring inducibility has been fused to a minimal promoter to generate a chimeric promoter responsive to chemical treatment. In this regard, the present invention seeks to provide a chimeric chemically inducible gene promoter sequence comprising a chemically inducible gene promoter sequence of the present invention.

Another aspect of the present invention is therefore to use the cis-elements to identify the transcription factors involved in inducible regulation. The transcription factors can then be manipulated to enhance inducibilty, for example a chimeric factor can be engineered with the addition of strong activators, such as the VP16 region from herpes simplex virus.

According to a first aspect of the present invention there is provided a chemically inducible gene promoter sequence comprising 897 base pairs immediately upstream of the transcription start point of the gene promoter sequence of the 27kD subunit of glutathione S-transferase.

According to a second aspect of the present invention there is provided a chemically inducible gene promoter sequence comprising 760 base pairs immediately upstream of the transcription start point of the gene promoter sequence of the 27kD subunit of glutathione S-transferase.

According to a third aspect of the present invention there is provided a chemically inducible gene promoter sequence comprising 570 base pairs immediately upstream of the transcription start point of the gene promoter sequence of the 27kD subunit of glutathione S-transferase.

According to a fourth aspect of the present invention there is provided a chemically inducible gene promoter sequence comprising 378 base pairs immediately upstream of the transcription start point of the gene promoter sequence of the 27kD subunit of glutathione S-transferase.

According to a fifth aspect of the present invention there is provided a chemically inducible gene promoter sequence having the sequence of the region 267 to 332 base pairs immediately upstream of the transcription start point of the gene promoter sequence of the 27kD subunit of glutathione S-transferase.

According to a sixth aspect of the present invention there is provided a chemically inducible gene promoter sequence having the sequence of the region 275 to 290 base pairs immediately upstream of the transcription start point of the gene promoter sequence of the 27kD subunit of glutathione S-transferase.

According to a seventh aspect of the present invention there is provided a chemically inducible gene promoter element having the sequence of the region 267 to 279 base pairs immediately upstream of the transcription start point of the gene promoter sequence of the 27kD subunit of glutathione S-transferase.

According to an eighth aspect of the present invention there is provided a chemically inducible gene promoter element having the sequence of the region 278 to 288 base pairs immediately upstream of the transcription start point of the gene promoter sequence of the 27kD subunit of glutathione S-transferase.

According to a nineth aspect of the present invention there is provided a chemically inducible gene promoter element having the sequence of the region 286 to 296 base pairs immediately upstream of the transcription start point of the gene promoter sequence of the 27kD subunit of glutathione S-transferase.

According to a tenth aspect of the present invention there is provided a chemically inducible gene promoter element having the sequence of the region 320 to 332 base pairs immediately upstream of the transcription start point of the gene promoter sequence of the 27kD subunit of glutathione S-transferase.

According to an eleventh aspect of the present invention there is provided a chemically inducible gene promoter sequence or element having substantial homology to the sequences defined above or a variant thereof.

According to a twelfth aspect of the present invention there is provided a DNA molecule comprising one or more of the sequences or elements of the present invention.

According to a thirteenth aspect of the present invention there is provided a multimer comprising more than one copy of any one of the above-defined chemically inducible gene promoter sequences or elements.

According to a fourteenth aspect of the present invention there is provided a chemically switchable gene construct comprising a sequence or element of the present invention operatively linked to a gene or series of genes whereby expression of the gene or the series of genes may be controlled by application of an effective exogenous inducer.

According to a fifteenth aspect of the present invention there is provided a plant having a construct according to the present invention integrated, preferably stably integrated within its genomic DNA by transformation.

According to a sixteenth aspect of the present invention there is provided a promoter/inducer combination wherein the promoter is the chemically inducible gene promoter sequence or the chemically inducible promoter element of the present invention.

According to a seventeenth aspect of the present invention there is provided an expression system for a plant, the expression system comprising a gene or a series of genes fused to a sequence or element of the present invention wherein the expression system is capable of being expressed in the plant and wherein expression of the gene or series of genes may be controlled by application of an effective exogenous inducer.

According to an eighteenth aspect of the present invention there is provided a transgenic plant comprising a gene construct or an expression system according to the present invention wherein the construct or expression system is integrated, preferably stably integrated, within the plant's genomic DNA.

According to a nineteenth aspect of the present invention there is provided the use of a sequence or element of the present invention to induce expression of a gene or a series of genes, when fused to the sequence or element, in a plant whereby expression of the gene or the series of genes may be controlled by application of an effective exogenous inducer.

According to a twentieth aspect of the present invention there is provided a process of expressing in a plant, a construct or an expression system according to the present invention wherein the expression system or construct is integrated, preferably stably integrated within the plant material's genomic DNA and whereby expression of the gene or series of genes may be controlled by application of an effective exogenous inducer.

DETAILED DESCRIPTION OF THE INVENTION

The chemically inducible promoter sequence or element is preferably immediately upstream of the transcription start point of the gene promoter sequence of the 27kD subunit of glutathione S-transferase, isoform II or upstream of the 27kD subunit of glutathione S-transferase, isoform IV.

Preferably, the chemically inducible promoter sequence or element is immediately upstream of the transcription start point of the 27kD subunit of maize glutathione S-transferase.

Preferably, the sequence encoding the gene promoter for the 27kD subunit of glutathione S-transferase, isoform II, is as shown in FIG. 1.

Preferably, the expression system comprises a gene construct according to the present invention.

A preferred embodiment of the present invention is a chemically inducible gene promoter sequence which is based on cis regulatory elements from the maize glutathione S-transferase 27, isoform II (GST-27-II) gene, as shown in FIG. 1, or which has substantial homology with that of FIG. 1 or a variant thereof, wherein the promoter sequence is operatively linked or fused to a series of genes whereby expression of the gene or series of genes may be controlled by application of an exogenous inducer.

An even more preferred embodiment of the present invention is a chemically inducible gene promoter sequence which is based on cis regulatory elements from the maize glutathione S-transferase 27, isoform II (GST-17-II) gene, as shown in FIG. 1, or which has substantial homology with that of FIG. 1 or a variant thereof, and which is integrated, preferably stably integrated, within a plant material's genomic DNA and wherein expression of a gene or series of genes may be controlled by application of an effective exogenous inducer.

The term "plant material" includes a germinating grain, or a seedling, a plantlet or a plant, or tissues or cells thereof (eg in the root, leaves and stem).

The term "substantial homology" covers homology with respect to at least the essential nucleic acids/nucleic acid residues of the promoter sequence or element providing the homologous sequence or element acts as a chemically inducible promoter. Preferably, there is at least about 70% homology, more preferably at least about 80% homology, and even more preferably there is at least about 90% homology with the chemically inducible promoter sequence or element of the present invention.

The term "a variant thereof" with reference to the present invention means any substitution of, variation of, modification of, replacement of, deletion of or the addition of one or more nucleic acid(s) from or to the promoter sequence providing the resultant sequence acts as a chemically inducible promoter. The term also includes sequences that can substantially hybridise to the promoter sequence.

The term "construct"—which is synonymous with terms such as "cassette", "hybrid" and "conjugate"—includes a gene or a series of genes directly or indirectly attached to the promoter sequence or element. The same is true for the term "fused" in relation to the present invention which includes direct or indirect attachment.

The term "expression system" means that the system defined above can be expressed in an appropriate organism, tissue, cell or medium. In this regard, the expression system of the present invention may comprise additional components that ensure to increase the expression of the gene or series of genes by use of the chemically inducible gene promoter or element. Also included in this term are transcription factors which are capable of binding to the chemically inducible promoter sequence or element.

The term "transgenic" in relation to the present invention—in particular in relation to the germinating seedlings and plants of the present invention—does not include a wild type promoter in its natural environment in combination with its associated gene or series of genes in its natural environment. Thus, the term includes seedlings or plants incorporating a gene or a series of genes which may be natural or non-natural to the seedling or plant in question operatively linked to the chemically inducible gene promoter sequence or element of the present invention.

The gene switch of the present invention, then, when linked to an exogenous or foreign gene and introduced into a plant by transformation, provides a means for the external regulation of expression of that foreign gene. The method employed for transformation of the plant cells is not especially germane to this invention and any method suitable for the target plant may be employed. Transgenic plants are obtained by regeneration from the transformed cells. Numerous transformation procedures are known from the literature such as agroinfection using *Agrobacterium tumefaciens* or its Ti plasmid, electroporation, microinjection or plants cells and protoplasts, microprojectile transformation, to mention but a few. Reference may be made to the literature for full details of the known methods.

Neither is the plant species into which the chemically inducible sequence is inserted particularly germane to the invention. Dicotyledonous and monocotyledonous plants can be transformed. This invention may be applied to any plant for which transformation techniques are, or become, available. The present invention can therefore be used to control gene expression in a variety of genetically modified plants, including field crops such as canola, sunflower, tobacco, sugarbeet, and cotton; cereals such as wheat, barley, rice, maize, and sorghum; fruit such as tomatoes, mangoes, peaches, apples, pears, strawberries, bananas and melons; and vegetables such as carrot, lettuce, cabbage, potatoes and onion. The switch is also suitable for use in a variety of tissues, including roots, leaves, stems and reproductive tissues.

One of the main advantages of the present invention as a result of the identification of smaller elements which can be used to achieve inducibility is that the smaller fragments are more convenient for vector development.

Another advantage of defining a core element is that it may be multimerised to enhance safener responsiveness.

A further advantage of using a core element is that it allows safener inducible chimeric promoters to be generated. This may include tissue specific or developmental promoters which could then be manipulated to become safener enhanced.

Another advantage is that such a core element may be optimised via a mutation strategy.

Defining a core element allows the isolation of the corresponding transcription factor by south western screening. This element could then be manipulated by mutation or over expression to achieve enhanced safener dependent expression.

The promoter may be induced by certain chemical compounds such as those shown previously in our International Patent Application No. WO90/08826, the disclosure of which is hereby incorporated by reference, known as "herbicide safeners", which can be applied, for example, as a spray, to the growing plant.

The following examples describe the identification of herbicide safener inducible cis regulatory elements within the GST-27 promoter. These have been identified by a combination of promoter deletion, in vivo footprinting, electrophoretic mobility shift assays, stable and transient reporter gene assays. This has defined specific fragments and a specific core element which have a number of utilities.

Various preferred features and embodiments of the present invention will now be described only by way of non-limiting example with reference to the accompanying Figures.

BRIEF DESCRIPTION OF THE DRAWINGS

FIG. 1 is a nucleotide sequence of the gene promoter sequence of the 27kD subunit of glutathione S-transferase, isoform II;

FIG. 2 is a circular map of plasmid pZM/RMS-3.

FIG. 14 shows partial sequences of retard probes for the GST-27 promoter and $ERE_1$. Footprinted G residues are shown underlined. The EFE element is based on the ethylene response element identified in the promoter of GST1 gene of carnation, which shows similarity to the elements identified in the GST-27 promoter (Itxhaki et al., 1994).

FIG. 17 shows the results of a competition assay wherein cold WT probes competed with hot WT290 Protein from uninduced leaves (0 hr.).

Promoter Isolation

The isolation and characterisation of the GST-27 promoter region is described in International Patent Publication No. W093/01294. In summary, a 205 bp hybridisation probe, corresponding to the 3' untranslated region of GST-27 cDNA, was amplified using PCR. The PCR product was random primed $^{32}$P-labelled and used to screen 5×10$^6$ recombinants from a maize genomic library (Zea mays cv. W22) in 1EMBL3 (Clontech). Plaque purifications were performed as described by Sambrook et al, 1989. 1EMBL3 DNA was isolated from genomic clones and used for restriction digest mapping and Southern blot analysis. A range of subclones were constructed into plasmid vectors including pG1E7 (3.9 kb EcoR I fragment into pBS (Stratagene)), pG1S15 (2.1 kb Sac I fragment into pBluescript KS (Stratagene)) and pG1X3 (2.2 kb Xho I in pBluesript KS). Plasmid pG1E7 was deposited on Jun. 14 1991 in the National Collections of Industrial and Marine Bacteria (NCIMB) under accession number NCIMB 40426. The nucleotide sequence of the GST-II-27 promoter is shown in FIG. 1.

The DNA sequence of the genomic subclones was determined by the dideoxy chain termination method using sequenase version 2.0 (USB) (Sanger et al, 1977). Oligonucleotide sequencing primers were prepared using an ABI DNA synthesiser Model 380B. DNA sequence data was analysed by the use PC/Gene and IG suite of the Intelligenetics molecular biology package.

Testing Deletions of the GST-27 Promoter in Transgenic Maize Plants

Figure 3:
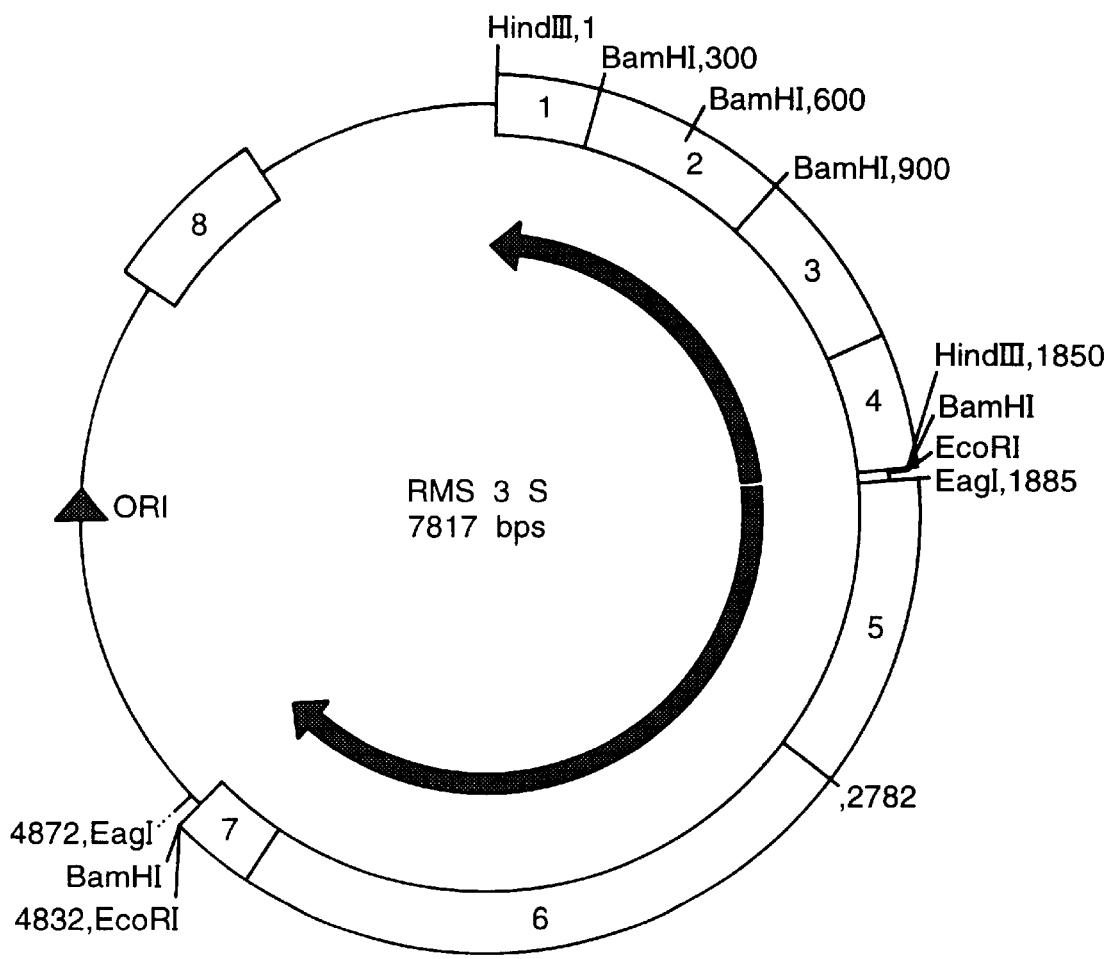
FIG. 3 is a circular map of plasmid pZM/RMS-3.

Standard recombinant DNA methods were adopted in the construction of plasmid vectors (Sambrook et al, 1989). A reporter gene construct containing a GST-27 3.8 kb EcoRI-Nde I 5' flanking region from pG1E7 was blunted ended and ligated into the Sma I site of the Agrobacterium Ti vector pTAK (Jefferson et al, 1987). The Nde I site, which lies at the predicted translation start codon of GST-27 was destroyed after blunting. This formed a convenient point for fusion with the E.coli UidA gene encoding b-glucuronidase (GUS) in pTAK. An EcoRI fragment containing 3.8 kb of the GST promoter GUS reporter gene and the nos terminator was isolated and subcloned in EcoRI cut pIJ109, a pUC19 based vector containing the PAT selectable marker cassette (CaMV 35S promoter, AdH I intron, phosphinothricin acetyl transferase (PAT), and the nos terminator), to form the maize transformation cassette pZMRMS3 (see FIG. 2). A deletion construct pZMRMS3S was generated containing 0.9 kb of GST-27 promoter, by removal of a 1.9 kb fragment (EcoRI-EagI) (see FIG. 3).

pZMRMS3 and pZMRMS3S were used to generate fertile transgenic maize plants by bombardment of embryonic cell suspensions (Fromm et al, 1990).

Plants were selected carrying the trans-gene using polymerase chain reaction (PCR). Genomic DNA for PCR analysis of transgenic plants was prepared. PCR was performed using the conditions described by Jepson et al (1991). Plants transformed with pZMRMS3 and pZMRMS3S were analysed with the primers GSTPCR 5'-CTCCCGTCGACCAAATACACT TGGT-3' (SEQ ID NO: 1) specific to the 3' region of GST-27 promoter and GUS 115 5'-GGATTCCGGCATAGTTAAAGAAATCAT-3', (SEQ ID NO: 2) specific to the 5' portion of the GUS gene.

Figure 4:
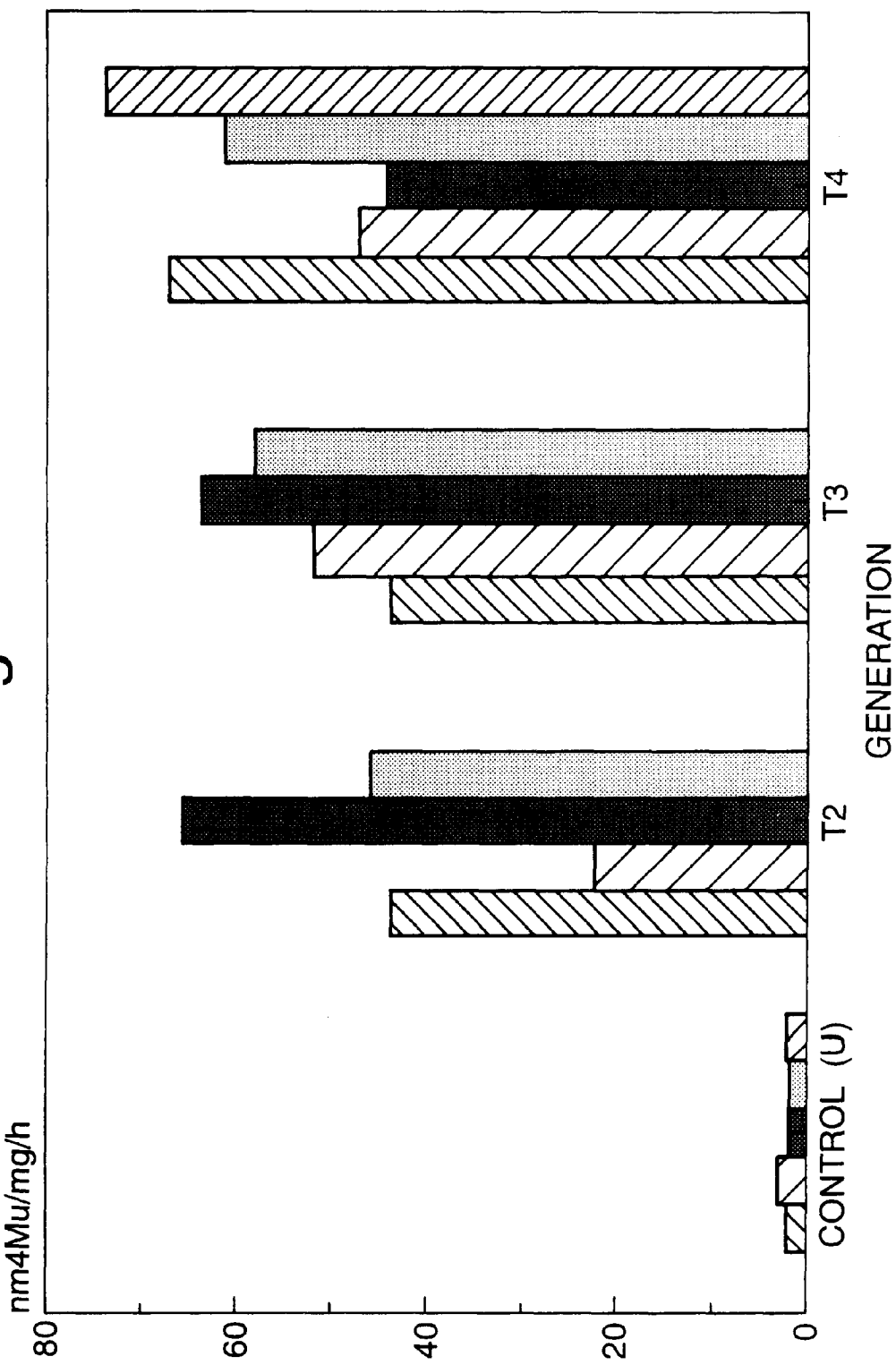
FIG. 4 is a graph showing the inducibility of pZM/RMS-3 and pZM/RMS-3-S in maize, and stability of expression in generation T2, T3 and T4
Figure 5:
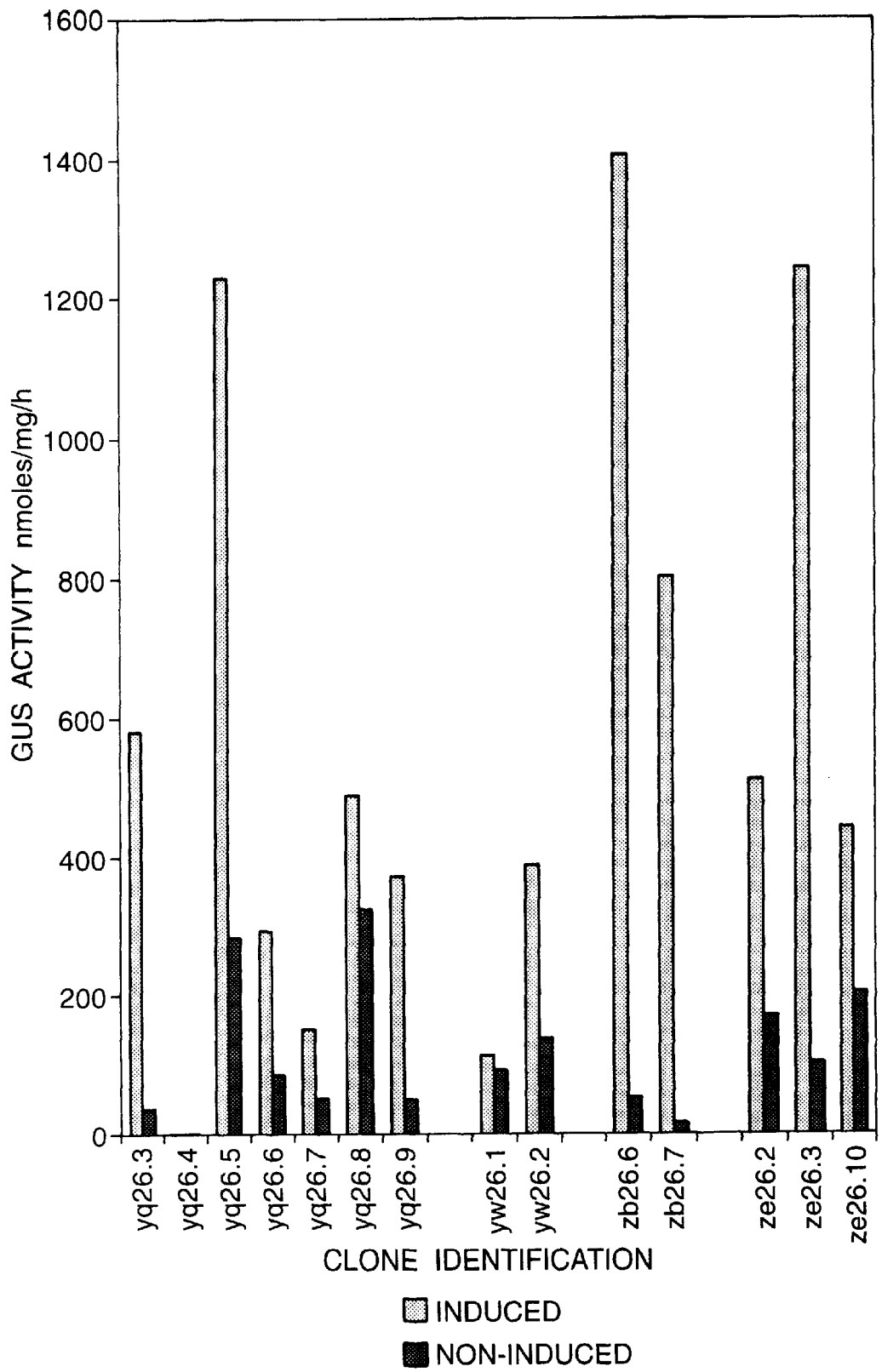
FIG. 5 is a graph showing the effect of treatment with safener on maize stably transformed with RMS-3-S.

To determine if both the 0.9 kb and 3.8 kb fragments retained inducible expression in transgenic maize, GUS enzyme assays were performed on leaf material in the presence or absence of safener. Induced tissue from mature glasshouse plants (16 H light/8 H dark cycle) was prepared by either leaf paint or spray application of 10 g/L R-29148 formulated in 81.5 g/L cyclohexanone, 3.3 g/L synperonic NPE 1800, 1.5 g/L tween 85. Fluorometric assays for GUS activity were performed with the substrate 4-methylumbelliferyl-D-glucuronide (Sigma) as described by Jefferson et al, 1987. Incubations were performed for 2 hours at 37° C. before being stopped with 0.2M sodium carbonate and fluorescence measured with a Perkin-Elmer LS-35 fluorometer. Protein concentration of tissue homogenates were determined by the Bio-Rad protein assay following the manufacturer's suggested procedure. FIGS. 4 and 5 demonstrate that both pZMRMS3 and pZMRMS3S retain inducibility.

Fine Deletion of the GST-27 Promoter

Figure 6:
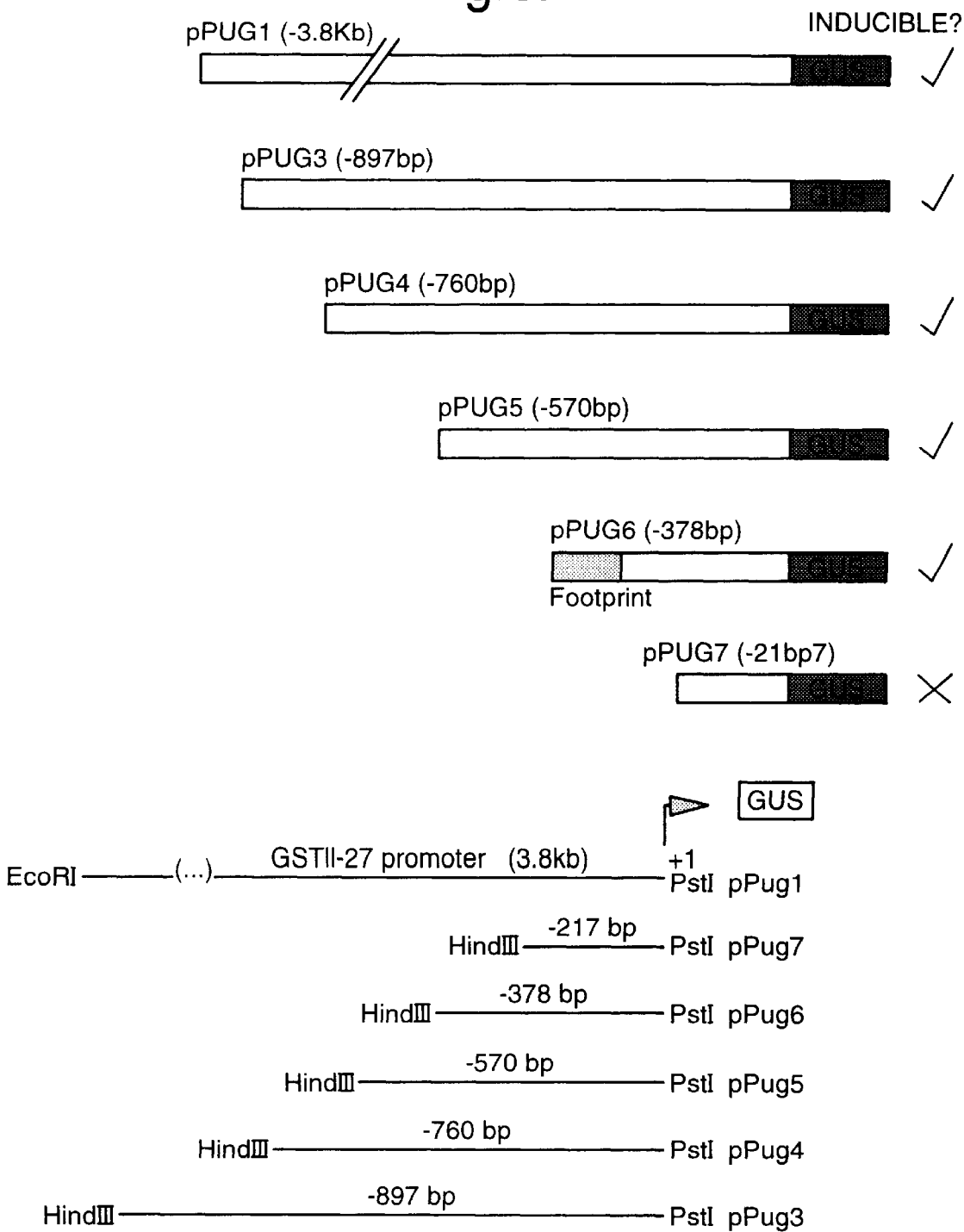
FIG. 6 shows plasmids pPUG1, pPUG3, pPUG4, pPUG5, pPUG6 and pPUG7. The 5' deletions of the GST II-27 promoter have been prepared from the original pPUG1 clone.

The preliminary deletion analysis generated in transgenic maize plants suggests that the elementis conferring inducibility must lie within the 900 bp immediately upstream of the transcription start point (TSP). A series of fine deletion constructs were made by fusing 200 bp deleted fragments of the 900 bp region to GUS marker gene. A Pst I site was identified adjacent to the transcription start point of the GST-27 promoter. A PCR primer AI2 was designed corresponding to this region (5' TGCCTGCTGCAGCTGCTACTTAT 3') (SEQ ID NO: 3). Primer AI2 was used in combination with 4 primers (AI3, AI4, AI5 and AI6)) all flanked with a Hind III site. AI3 (5' GTTAAAGCTTCGCAAGTCGCACCCCACTA 3') (SEQ ID NO: 4), AI4 (5' CTGAAAGCTTCGGTGCACCGAAT 3') (SEQ ID NO: 5), AI5 (5' GCGGCAAGCTTAATATGTGATGATGATA 3') (SEQ ID NO: 6) and PI6 (5' TTACAAGCTTCGCAAGTATCGGTAGGCAT 3') (SEQ ID NO: 7) were used in PCR experiments with AI3 to generate fragments of 217 bp, 378 bp, 570 bp and 760 bp respectfully. The PCR products produced were cut with Pst I and Hind III and the fragments cloned into pZMRMS3 cut with Pst I and Hind III. The resultant vectors pUG4, pUG5, pPUG6 and pPUG7 are shown in FIG. 6.

Figure 7:
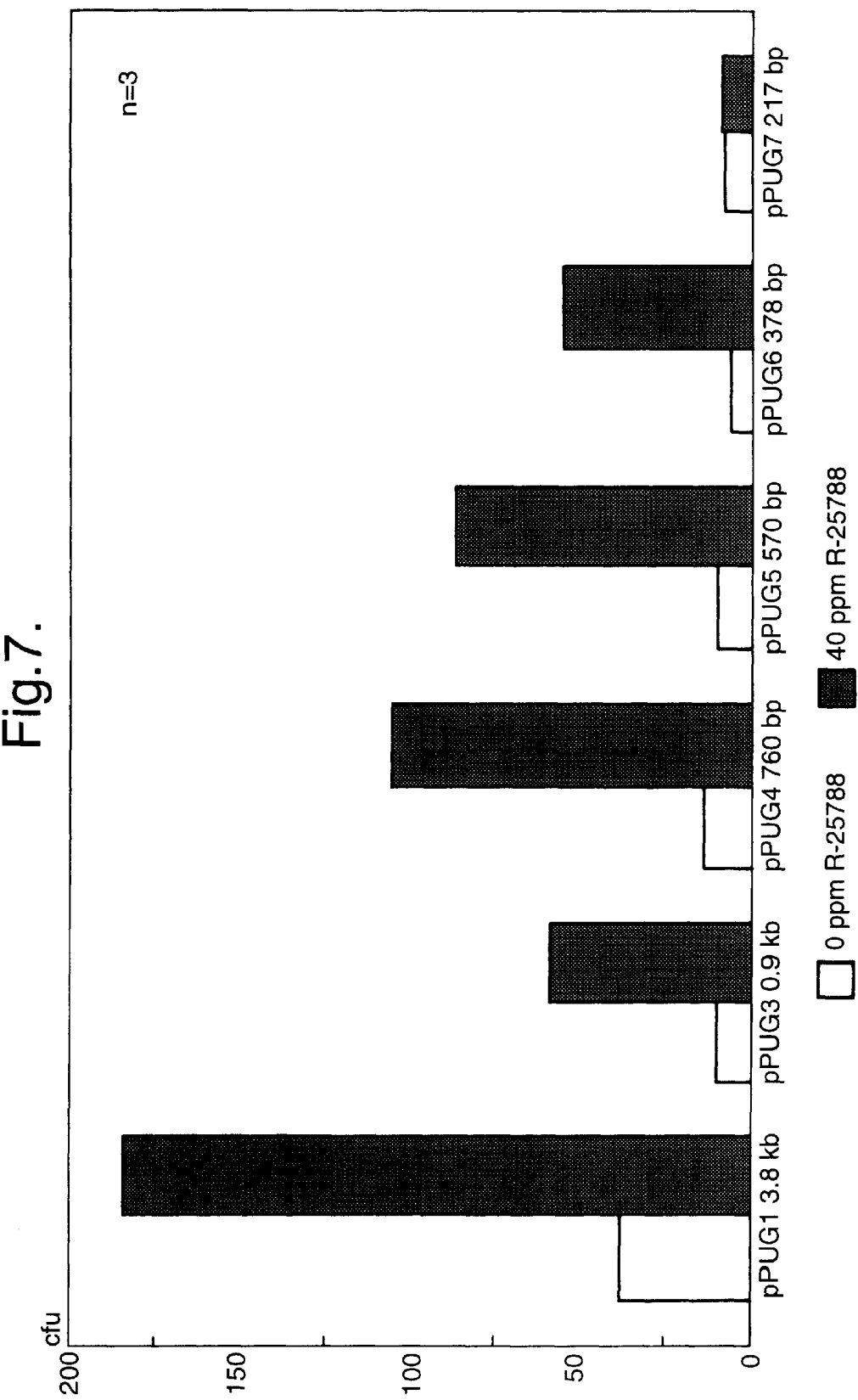
FIG. 7 shows a graph of the results of a test of the inducibility by R-25788 for the 5' deletion constructs of the GST II-27 promoter.

Transient transformation assays were performed with the pPUG vectors in BMS (Black Mexican Sweet) suspension cells, grown in the presence or absence of safener (dichlormid 40 ppm). DNA was delivered using silicon carbide whisker transformation (Wang et al, 1994). Promoter activity was scored by counting colour forming units. FIG. 7 reveals all the pPUG constructs were inducible, except for one containing only 217 bp (designated pPUG7) of the promoter. A construct containing 378 bp (designated pPUG6) still conferred inducibility. This data suggests that the inducible element/s lay between −217 and −378 bp upstream of the transcription start point.

Mapping Inducible Elements within the GST-27 Promoter Using in-vivo Footprinting In vivo footprinting (see method below) was used to detect proteins interactions with the promoter and so locate the element which confers inducibility. Dimethyl sulphate (DMS) is used to modify guanine residues in-vivo by methylating the N7 position. If a protein is closely associated with the DNA this reaction will be inhibited and so DNA-binding factors can be mapped to the bases involved. After DMS treatment the DNA is amplified and sequenced. Contact points are identified on genomic autoradiographs as G residues that are less intense when compared to the lane of uninduced DNA.

Figure 8:
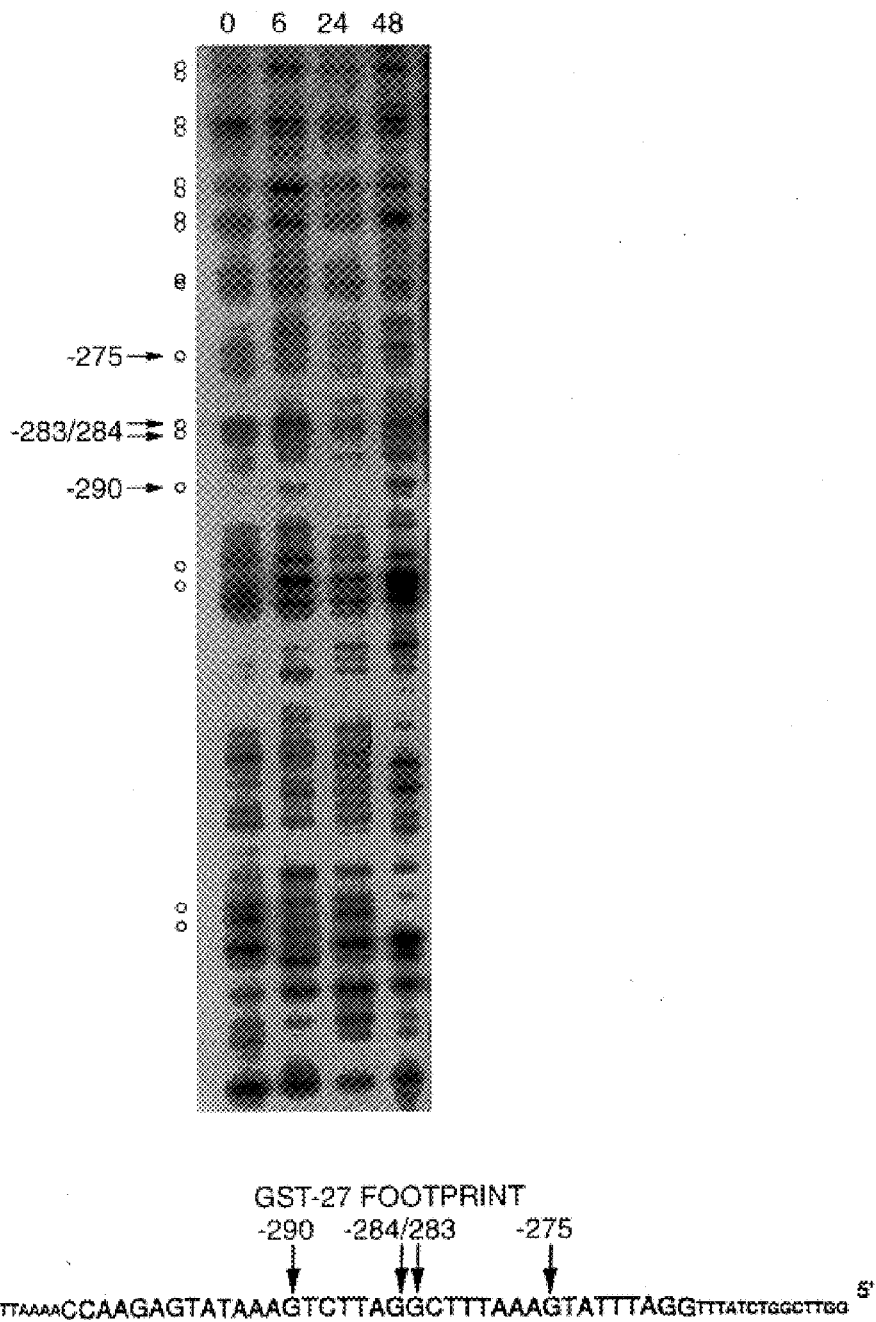
FIG. 8 shows an in vivo footprint of the bottom strand of the GST-27 promoter. DNA was extracted from maize leaves treated with DMS in vivo 0, 6, 24 and 48 hours after induction of GST-27 with diclormid and used for in vivo footprinting. Open circles indicate the position of guanine residues. Residues which are protected at 24 hours are indicated by arrows and numbered according to their position relative to the TSP.

Primers were designed so that the area between −217 and −378 could be analysed using this method. A maize plant was treated with safener to induce expression of GST-27. In-vivo footprint analysis was performed before the treatment (0 hours) and at 6, 24 and 48 hours after treatment. Results are shown in FIG. 8. It can be seen that a protein binds to a G residue at position −290 at 24 hours after the plant has been treated with safener (no band visible) but not at 0, 6 or 48 hours (band visible). Positions −275, −283 and −284 also have fainter bands at 24 hours. This result is reproducible. In short we have identified 2 putative elements which appears to bind protein factors in a safener dependent manner.

Figure 9:
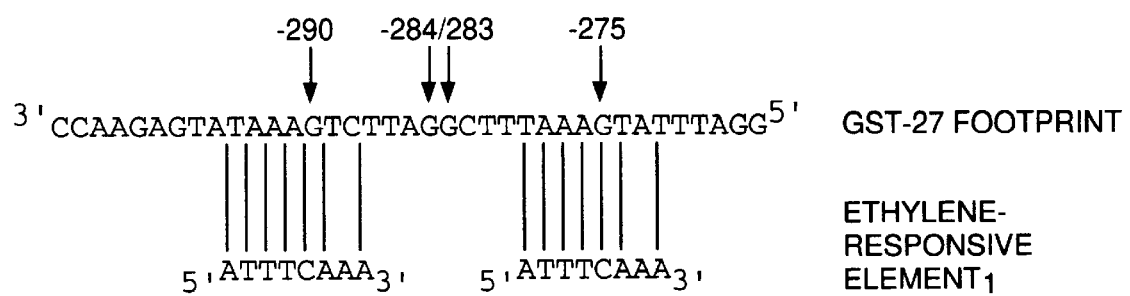
FIG. 9 shows the maize GST-27 footprint to be complementary to a carnation GST-1 ethylene-responsive element 1. W. R. Woodson et al., Proc. Nat't Acad. Sci. USA Bol. 91, pp. 8925–8929, Sep. 1994.

These elements share homology with each other. In addition it is interesting to note that the homologous regions are complementary to a known ethylene responsive element in the GST1 gene in carnation (Itzhaki et al, Proc. Natl. Acad. Sci. USA Vol. 19, 8925–8929, 1994) as shown in FIG. 9.

Protocol for In-vivo Footprinting of Maize Leaves:
(Modified from Hammond-Kosack and Bevan, Plant Mol. Biol. Reporter, Vol. 11, No. 3, Sep. 1993)

1. In-vivo DMS treatments applied for 1 minute and then slowly released. After 5 minutes the medium was removed and the tissue was washed several times in MS media. The tissue was blotted dry and stored at −70° C. until all time points (0, 6, 24 and 48) hours were collected.

2. Preparation of chromosomal DNA:
The frozen DMS treated tissue was crushed to a fine powder using a pestle and mortar and liquid nitrogen. 30 ml hot (65° C.) extraction buffer (100 mM Tris HCl pH 8.0, 50 mM EDTA pH 8.0, 50 mM NaCl, 1.25% SDS, 8.3 mM NaOH, 0.38 g/100 ml Na bisulphite) was added, mixed and incubated for 15 minutes at 65° C. 6.16 ml 5M KAc were added and then the sample was incubated on ice for 20 minutes. After centrifugation at 3.5K for 5 minutes the supernatant was filtered through Miracloth and 0.7 vols propan-2-ol were added. This was spun at 4K for 10 minutes, the pellet was washed twice in 70% ethanol and then resuspended in 0.84 ml T5E and 0.36 ml 10M NH4Ac. This solution was spun for 5 minutes at 13K. The supernatant was precipitated with 0.73 ml propan-2-ol.

The pellet was precipitated once more before dissolving in 100 ml T10E. The DNA was digested with Hind III.

3. Ligation-mediated PCR (LMPCR):
The DNA samples were amplified using LMPCR. 3 nested primers were designed to amplify both strands of the GST-27 promoter between 0 and 350 bp upstream of the TSP. The 1st primer for each strand was annealed and then extension to the end of the molecule was allowed to occur. A linker of known sequence was annealed to the end of each extended molecule. Normal PCR was then carried out using a primer specific for the linker and the 2nd of the nested primers. When amplified the DNA molecules were labelled using the 3rd primer incorporating an end-label. The samples were phenol-chloroform extracted, propan-2-ol precipitated and resuspended on sequencing loading buffer. To visualise the footprint the samples were run in a 6% sequencing gel.

Electrophoretic Mobility Shift Assays (EMSA):
This method was used to test the hypothesis that the in-vivo footprinted areas could bind specific nuclear proteins in-vitro. Short radiolabelled fragments (probes) of a promoter will migrate through an electrophoresis gel at a speed determined by their size and charge. If a probe has a protein associated with it the migration will be retarded. On an autoradiograph this will be visualised as a band which is not present in the absence of protein. Competition assays with cold probes determine if binding is specific.

Figure 10:
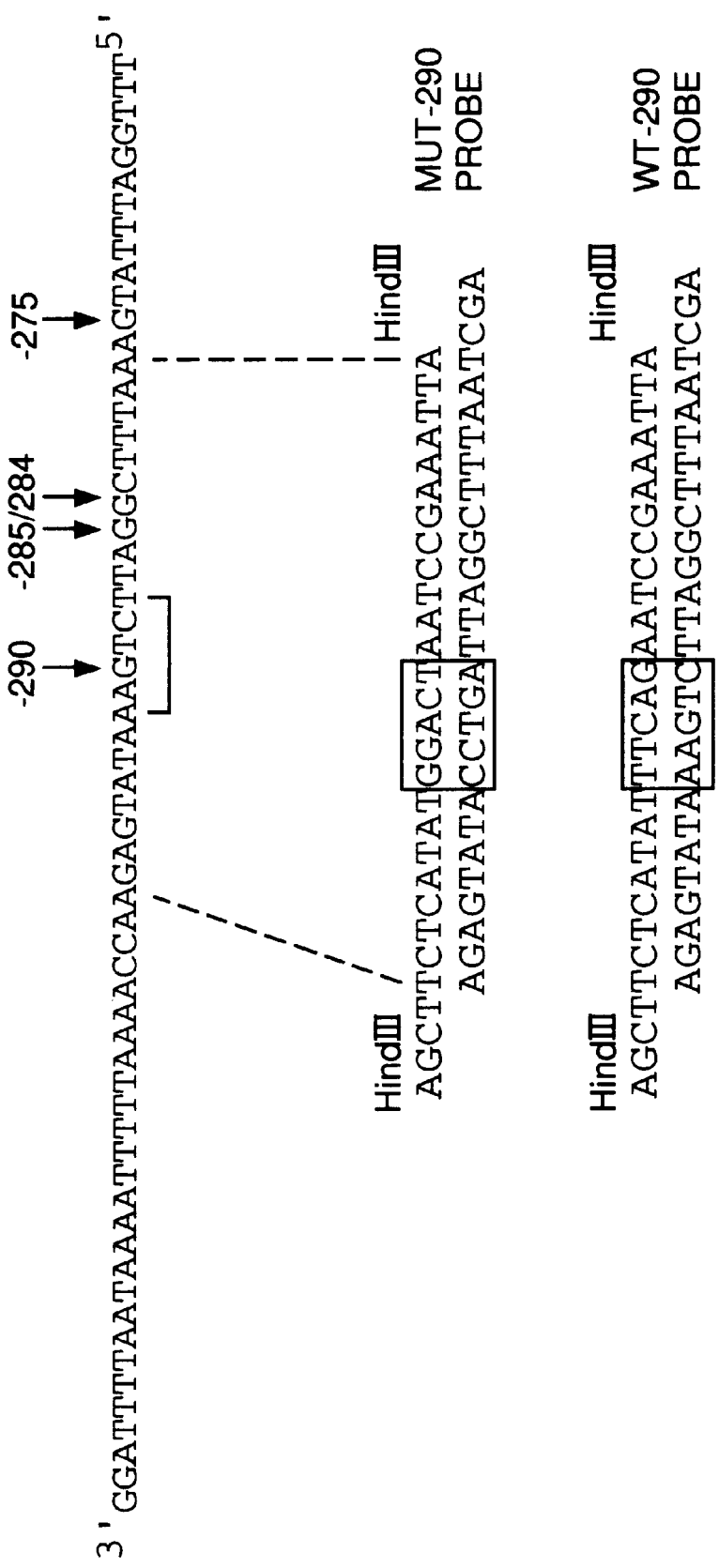
FIG. 10 shows retard probes for a G290 footprint.

Nuclear protein extracts were made from induced and non-induced maize leaves. Two short (25 bp) probes (see FIG. 10) were made to incubate with the protein:

1. WT290—covering the −290 and −283/284 footprinted area
2. MUT290—as 1 but including a 5 bp mutation around −290.

Figure 11:
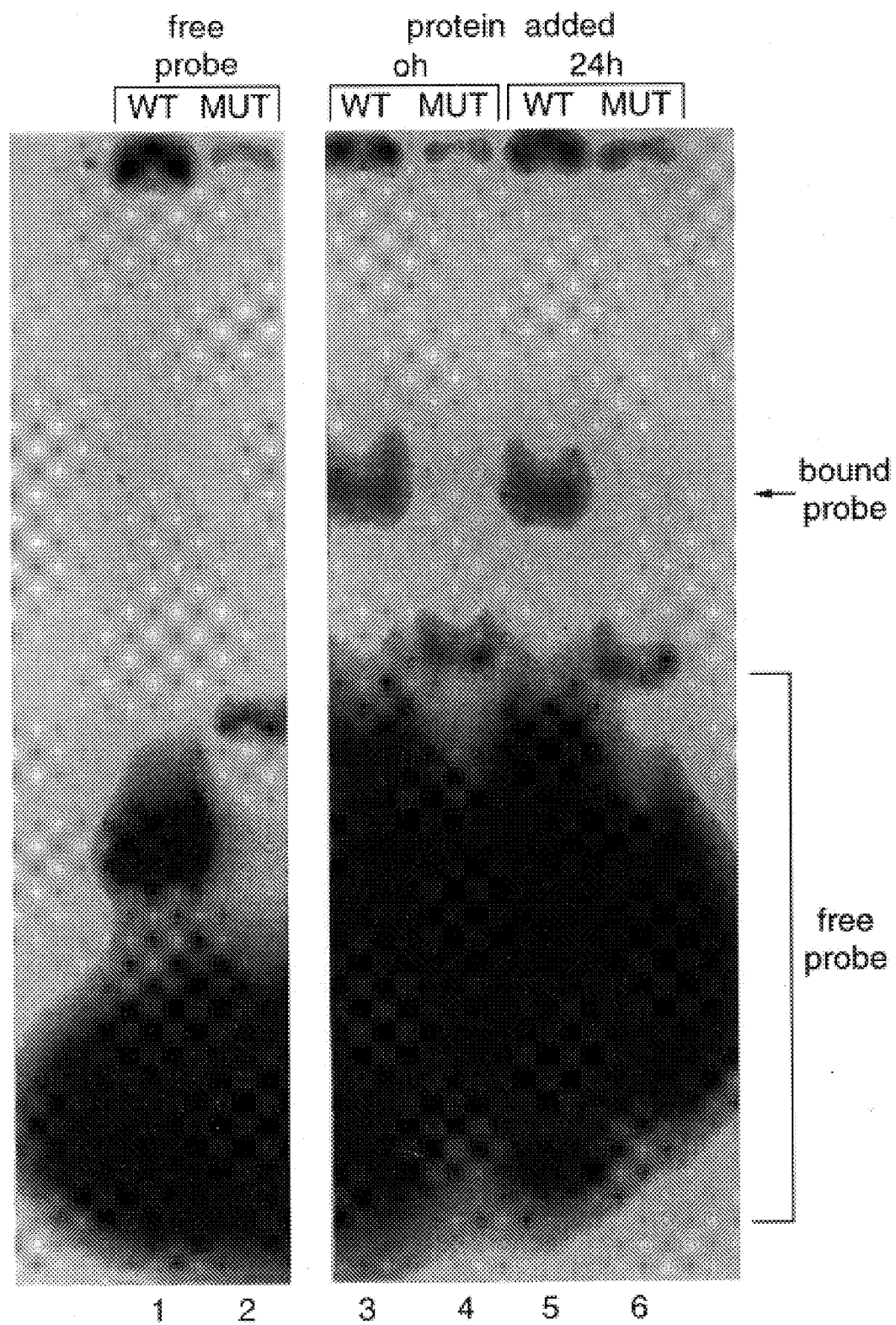
FIG. 11 shows an autoradiograph of EMSA using WT290 and MUT290 probes. 1 µg nuclear protein extract was incubated for 20 minutes at room temperature with 20000 cpm of the appropriated probe, 1 µg poly d(I-C), 5 mM DTT, 50 mM KCl, 100 mM Mg $Cl_2$ in 10 µl of binding buffer. Lanes 1 and 2 contain free probe with no protein added. Lanes 3 and 4 contain probes incubated with nuclear protein from uninduced leaves. Lanes 5 and 6 contain probes with nuclear protein from induced leave. The positions of the free and bound probe are indicated.
Figure 12:
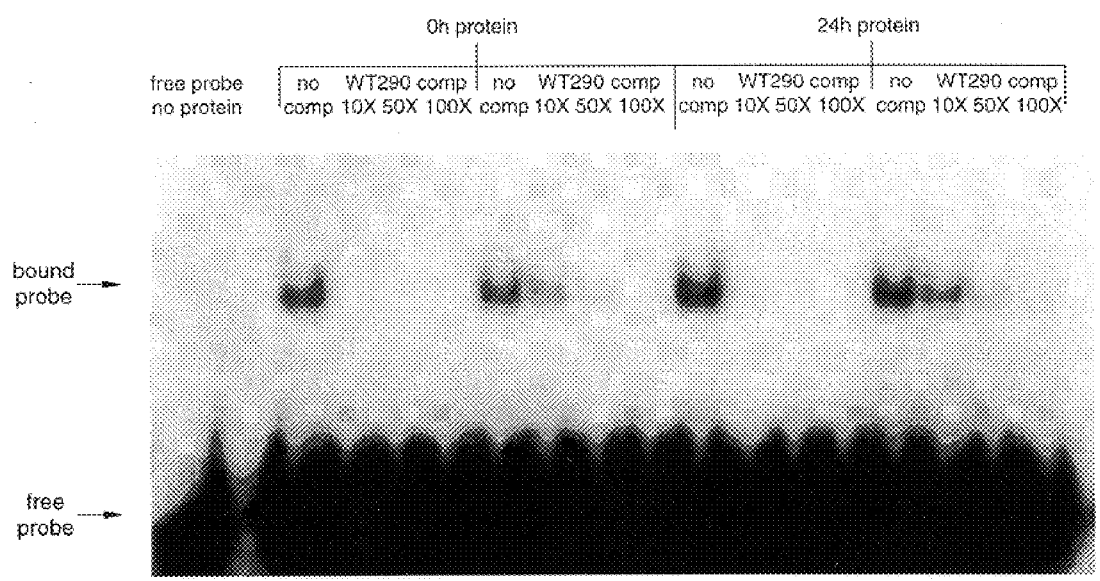
FIG. 12 shows an autoradiograph of an EMSA competition assay 1 µg nuclear protein extract was incubated for 20 minutes at room temperature with 0.5 ng (20000 cpm) of WT 290 probe, 1 mg poly d(I-C) 5 mM DTT, 50 mM KCl, 100 mM $MgCl_2$ in 10 µl of binding buffer. Protein; from uninduced leaves was added to samples in lanes 2 to 9 and from induced leaves from lanes 10 to 17. Cold WT 290 competitor of the indicated amounts was added to samples in lanes 3 to 5 and 11 to 13. Likewise cold MUT 290 competitor was added to samples in lanes 7 to 9 and 15 to 17. As a comparison no competitor was added to samples in lanes 2, 6, 10, or 14. Lane 1 represents WT 290 probe with no added protein. The positions of the bound and free probe are indicated.

Results are shown in FIG. 11. The WT probe binds a protein (band visible in lanes 3 and 5). The mutation in MUT290 abolishes binding (weaker band in lanes 4 and 6). The pattern is identical whether the nuclear protein extract is from induced or non-induced leaves. Therefore the binding protein must always be present. In-vivo this protein must be modified such that binding only occurs when the gene is induced. FIG. 12 represents the results of competition assays. Cold WT290 probe successfully competes with radiolabelled WT290 probe to bind the protein resulting in loss of the band (lanes 2, 3, 4 and 10, 11, 12). This effect is not seen when cold MUT290 is added (lanes 6, 7, 8 and 14, 15, 16). Therefore the binding seen is specific.

Figure 15:
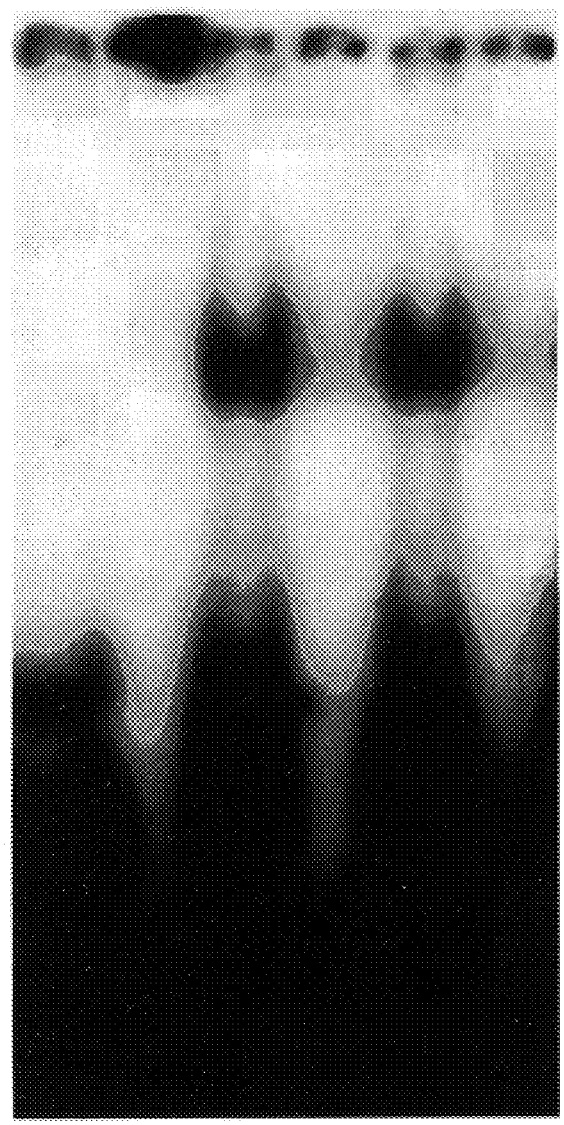
FIG. 15 shows retard using WT and MUT probes of G275.
Figure 16:
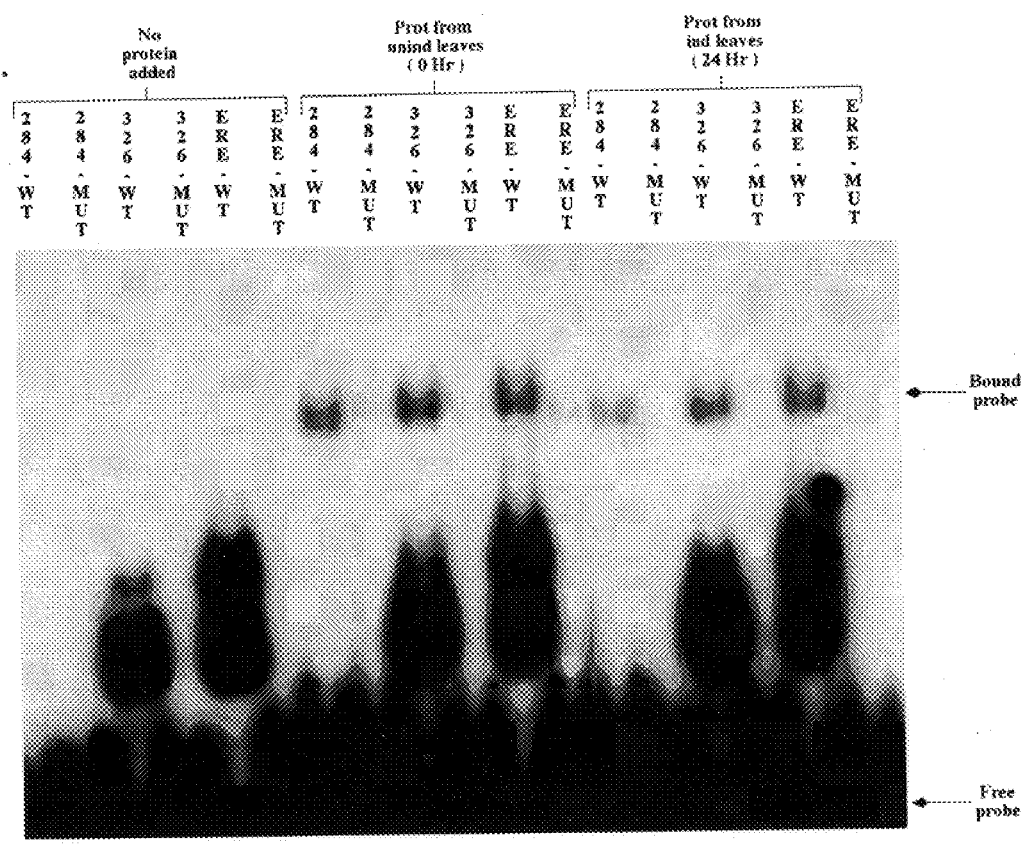
FIG. 16 shows retard using WT and MUT probes of G326, G284 and the ERE.

In addition to the 290 region, it has also been demonstrated that the −275 region (see FIG. 14), is involved in transcription factor binding. FIG. 15 shows the results of an EMSA in which the 275 probe binds while the mutated 275 element fails to bind transcription factors. In a subsequent experiment the 284 and 326 (see FIG. 14) regions have been shown to be involved with binding of protein from uninduced and induced nuclear extracts (see FIG. 16). Competition assays (see FIG. 17) with the 275, 284, 290, and 326 regions show that the binding observed in the EMSA study is specific. The various mutated and wild probes used in the EMSA study are listed below:

Probe name Sequence
290WTN 5 AGCTT GC TATTCAGAAT GC A3 (SEQ ID NO: 8)
    3 A CG ATAAAGTCTTC AG TTCGA 5 (SEQ ID NO: 9)
290MUTN5 5 AGCTT GC TATGGCCTAAT GC A3 (SEQ ID NO: 10)
    3 A CG ATACCTGATTA CG TTCGA 5 (SEQ ID NO: 11)
284WTN 5 AGCTT GC GAATCCGAAAT GC A3 (SEQ ID NO: 12)
    3 A CG CTTAGGCTTTA CG TTCGA 5 (SEQ ID NO: 13)
284MUTN6 5 AGCTT GC GACGAATCAAT GC A3 (SEQ ID NO: 14)
    3 A CG CTGCTTAGTTA CG TTCGA 5 (SEQ ID NO: 15)
275WTN 5 AGCTT GC AATTTCATAAA GC A3 (SEQ ID NO: 16)
    3 A CG TTAAAGTATTT CG TTCGA 5 (SEQ ID NO: 17)
275MUTN5 5 AGCTT GC AATGGACGAAA GC A3 (SEQ ID NO: 18)
    3 A CG TTACCTGCTTT CG A 5 (SEQ ID NO: 19)
326WTN 5 AGCTT GC GGTTCCTAAAA GC A3 (SEQ ID NO: 20)
    3 A CG CCAAGGATTTT CG TTCGA 5 (SEQ ID NO: 21)
326MUTN6 5 AGCTT GC GGCGGAAGCAAAGC A3 (SEQ ID NO: 22)
    3 A CG CCGCTTCGTTT CG TTCGA 5 (SEQ ID NO: 23)
ERE-WT 5 AGCTT GC TATTTCAAAAT GC A3 (SEQ ID NO: 24)
    3 A CG ATAAAGTTTTA CG TTCGA 5 (SEQ ID NO: 25)
ERE-MUT 5 AGCTT GC TATGGTCCAAT GC A3 (SEQ ID NO: 26)
    3 A CG ATACCAGGTTA CG TTCGA 5 (SEQ ID NO: 27)

These data taken together with the in vivo footprinting data indicate that this region of the GST-27 promoter is involved in chemical dependent binding of transcription factors leading to gene activation.

Protocol for Electophoretic Mobility Shift Assays (EMSAs):
    (modified from Watson and Thompson, Meth. Enzymol. Vol. 118, pp. 57–75, 1986 and Holdsworth and Laties, Planta, Vol. 179, pp. 17–23, 1989)

1. Preparation of nuclear protein extracts from maize leaves:
    A 1% solution of R-29148 safener was applied to the upper and lower surfaces of 3 week old maize leaves. 15 g of material was harvested at 0 and 24 hours. The tissue was crushed to a fine powder using a pestle and mortar and liquid nitrogen. The tissue was divided into 2; to each sample 70 ml extract buffer (0.25M sucrose, 10 mM NaCl, 10 mM MES-NaOH pH 6.0, 5 mM EDTA, 0.15 mM spermine, 0.5 mM spermidine, 0.2 mM PMSF, 10 mM NaF, 20 mM b-ME, 0.1% BSA, 0.6% non-idet P40) was added. The homogenate was filtered through 3 layers Miracloth to a corex tube. A 25% Percoll cushion was added to the bottom of the tube. This was spun at 3K in a swing bucket rotor at 4° C. for 30 minutes. Nuclei were collected from the bottom of the tube and resuspended in extract buffer (not including BSA). The sample was spun at 5K for 5 minutes at 4° C. The nuclei were resuspended in 100 ml dialysis buffer (40 mM KCl, 24.7 mM HEPES-NaOH pH 7.9, 5 mg/ml leupeptin, 5 mM EDTA, 5 mg/ml antipain, 1 mM DTT, 25% glycerol, 10 mM NaF). A ⅒th volume of ammonium sulphate was added and the sample incubated on ice for 30 minutes, then spun at 13K for 20 minutes. 1.5 volumes of ammonium sulphate were added to the supernatant which was incubated on ice for 60 mins and then spun at 13K for 20 minutes. The sample was resuspended in 100 ml dialysis buffer and dialyed in the buffer for 2×2 hours. The protein concentration in the final sample was measured using Bradford's assay.

2. EMSA:
    1 mg protein extract was incubated for 20 minutes at room temperature with 20000 cpm (c. 0.5 ng) probe (labelled by filling in the 3' recessed termini with labelled dNTPs using Klenow), 1 mg poly d(I-C), 5 mM DTT, 50 mM KCl, 100 mM MgCl$_2$ in 10 ml binding buffer (250 mM HEPES pH7.6, 10 mM EDTA, 50% glycerol). The samples were loaded on a 6% olyacrylamide gel run in 0.25× TBE buffer.

Transient Expression Assays

To test that the footprinted areas indicate the positions of inducible elements transient assays were performed. By mutating the putative inducible elements to prevent trans-acting protein factors binding, inducibility should be lost. A construct (pPUG5) containing 570 bp of the promoter fused to GUS was previously shown to retain inducibility. This was mutated, using anchored PCR, in the areas that had been footprinted. Three constructs were made, each containing a 10 bp mutation:
1. MUT290 containing a 10 bp mutation around G-290
2. MUT284 containing a 10 bp mutation around G-284
3. MUT326 containing a 10 bp mutation around G-326

Figure 13:
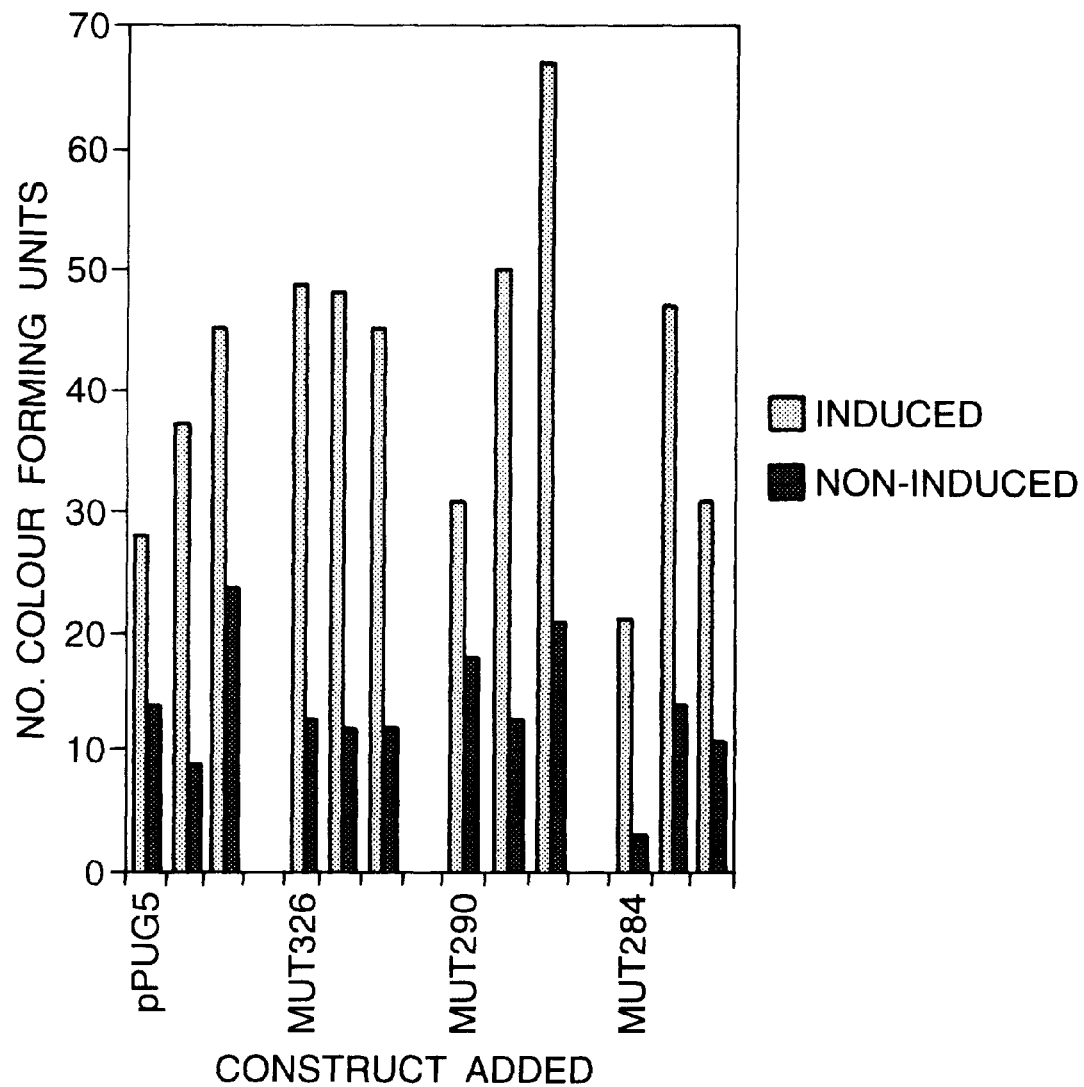
FIG. 13 shows the results of a transient transformation assay of pPUG5 mutations. 500 µl of BMS cells (50% packed cell volume) were transferred with 10 µg plasmid DNA. Assays using each plasmid were carried out in triplicate under 2 conditions. 1 Induced media containing 40 ppm safener R-25788. 2 Uninduced media pPUG5 contains 570 bp of the GST-27 promoter and is known to retain inducibility. The 3 mutated constructs are sumilar to pPUG5 but each contains a 10 bp mutation around G residues which were footprinted at 24 hours after induction.

The MUT326 construct was made as a convincing footprint was seen at 48 hours involving G-325/326. The constructs were transformed into BMS suspension cells using the silicon fibre so-called whisker technique as described in our U.S. Pat. No. 5,302,523. Results are shown in Table 1 (FIG. 13). The mutated constructs were still inducible. The fold induction for all constructs was comparable to that of WT pPUG5.

Following this result a homology search was performed on the 570 bp fragment in pPUG5 to identify any duplication of the putative elements. If multiple elements are present the effect of mutating one may not be visible. No direct duplications were found. However, it was observed that there was high (67%) homology within the fragment. From the data it is believed that a duplication and inversion event involving 150 bp had occurred. In addition, as the −290 and −275 footprinted region show significant homology the transient assay experiment was repeated in the pPUG6 (378 bp) backround promoter, with all three mutaions in the same vector.

Plant Transformation Vectors
PCR-mediated Mutagenesis of GST-27 Promoter

Four primers were required for PCR-mediated mutagenesis, the primers used are listed below:
Primers Used to Create 3XMUT in pPUG6:
R1=5' CTGAAAGCTTCGGTGCACCGAAT 3' (SEQ ID NO: 28) (pAI4)
R2=3' TATTCATCGTCGACGTCGTCCGT 5' (SEQ ID NO: 29) (pAI2)
M=5' CCTAAAATTATTTTAAAAATTTTGGT-TCTCATATGGACTACGAATCAA TGGACGAAATCCAAATAGACCG 3' (SEQ ID NO: 30)
rev=3' GGATTTTAATAAAATTTTTAAAACCAAGAGT 5' (SEQ ID NO: 31)

Primers R1 and R2 flank the promoter on either side of the region which is to be mutated and contain suitable enzyme restriction sites for cloning. The 5' and 3' ends of primer M are identical to the promoter while the middle section contains the altered sequence. Primer rev is identical to the wild type 5' end of primer M.

In step 1, two PCRs were performed in a volume of 25 μl with 20 ng wild type template plasmid, 10X PCR buffer, 2.5 μl 2 mM dNTPs, 2 μl 20 mM primer R1 or M, 2 μl 20 mM primer rev or R2 and 0.25 μl Amplitaq (Perkin Elmer). The program used was 94° C. for 2.5 minutes followed by 30 cycles of 94° C. for 1 minute, 50° C. for 1 minute and 72° C. for 1 minute. The reactions were each carried out 4 times to generate enough product for step 2. The resulting fragments R1/rev and M/R2 were purified and quantified.

In step 2, the fragments R1/rev and M/R2, which share a region of overlapping sequence, were annealed. 250 ng of each fragment were mixed in a 25 μl volume with 10X PCR buffer, 2.5 μl 2 mM dNTPs and 0.25 μl Amplitaq. Annealing and then extension of the annealed product were performed using the program 94° C. for 2.5 minutes followed by 9 cycles of 94° C. for 1 minute, 40° C. for 1 minute and 72° C. for 1 minute.

In step 3, the extended heterodimers, comprising of the whole promoter sequence containing the mutation, were amplified by the addition of primers R1 and R2. To the same reaction from step 2, 2.5 μl 10X PCR buffer, 2.5 μl 2 mM dNTPs, 2 ml 20 mM R1, 2 ml 20 mM R2, 15.75 μl of water and 0.25 μl Amplitaq were added. PCR was carried out using the same program as that which was used in step 1. The resulting fragment was purified and cloned into pGEM-T vector (Promgea) and sequenced to ensure that the correct bases were mutated. 3XMUTBin/6 contained 5 bp mutations to the footprinted G residues G-290, G-283/284 and G-275 and their flanking nucleotides.

A similar strategy was adopted to generate 4 mutations in the pPUG6 background using the primers given below.
Primers Used to Create 4XMUT in pPUG6:
R1=5' CTGAAAGCTTCGGTGCACCGAAT 3' (SEQ ID NO: 32) (pAI4)
R2=3' TATTCATCGTCGACGTCGTCCGT 5' (SEQ ID NO: 33) (pAI2)
M=5' GTCTATTCAGGTTCGGGGAAGCAAATTAT 3' (SEQ ID NO: 34)
rev=3' CAGATAAGTCCAAG 5' (SEQ ID NO: 35)

Further PCR mediated mutagenesis was performed using p3XMUT/PUG6 as template DNA in order to mutate the footprinted G residues G-325/236 and four flanking nucleotides. The 4XMUTBin/6 contained 5 bp mutations to the footprinted G residues G-290, G-283/284, G-275 and G-325/326 and their flanking nucleotides.

The mutated fragments were introduced into the GST-27 promoter by cutting the pGEM-T vectors with HindIf and PstI and cloned into pPUG6 which had been linearised with the same enzymes. In this way the wild type promoter in pPUG6 was removed and replaced with the 3XMUT or 4XMUT version, so creating the plasmid p3XMUT/PUG6 or p4XMUT/PUG6. This was cloned into pBin400 using the same strategy as described above for the wild type pPUG6 plasmid, to form 3XMUT/Bin6 or 4XMUT/Bin6.

Vector Construction

Tobacco plants were transformed with five constructs, all of which were based on the binary vector pBin400 (Spychalla and Bevan, 1993). Three 5' deletions of the GST-27 promoter fused to the reporter gene GUS were prepared, containing 570, 378 and 217 bp of the promoter upstream from the TSP. These truncated promoter:GUS fusions were present in the constructs pPUG5 (570 bp), pPUG6 (378 bp) and pPUG7 (217 bp). The truncated promoters fused to GUS were cut out on a HindIII, EcoRI fragment from these three plasmids and cloned directly into pBin400, which had been linearised with the same enzymes. The resulting constructs were named pBin/5, pBin/6 and pBin/7. Also transformed were 3XMUT/Bin6 and 4XMUT/Bin6.

Transformation of Agrobacterium

An overnight culture of A.tumefaciens (strain T37SE) was set up in 10 mls YEP broth (1% (w/v) Bactopeptone [Difco], 1% (w/v) yeast extract [Difco], 0.5% NaCl) with 50 μg/ml kanamycin sulphate and grown at 30° C. Four mls of this were used to inoculate 100 mls YEP broth, containing 50 μg/ml kanamycin sulphate, which was grown for 4–5 hours. The cells were pelleted at 2,500 rpm for 10 minutes (Sorvall RC3C centrifuge, H6000A rotor), resuspended in 2 mls YEP broth and chilled on ice for 5 minutes in 200 μl aliquots. Ten microlitres pBin DNA at 0.1–0.2 μg/ml were added to the cells. The cells were immediately frozen in liquid nitrogen for about 15 seconds followed by a heat shock of 37° C. for 5 minutes. 1 ml YEP was then added and the cells grown at 30° C. for 1–2 hours. A 100 ml aliquot from each transformation was spread onto YEP plates (YEP with 1.5% (w/v) agar) containing 50 μg/ml kanamycin sulphate to select for the Agrobacterium and 50 μg/ml spectinomycin hydrochloride to select for the binary vector. The plates were inspected for growth after 48 hours incubation at 30° C. Single colonies were streaked out on Minimal T plates (350 mls water agar [1.5% (w/v) agar], 20 mls 20× salts, 20 mls 20× T buffer, 20% glucose), containing the selecting antibiotics, and grown for 3 days at 30° C. Bacterial colonies from these plates were used to inoculate liquid cultures for DNA preparation.

Plasmid DNA Preps from Agrobacterium, Tumefaciens

Ten mls YEP broth, containing antibiotic to select for the binary vector and the Agrobacterium, were inoculated with a single colony of A. tumefaciens and grown overnight at 30° C. The cells were collected by centrifugation at 2,500 rpm for 20 minutes (Sorvall RC3C. centrifuge, H6000A rotor), then resuspended in 200 ml ice-cold solution I (Horsch et al 1985) and allowed to stand for 30 minutes at room temperature and then vortexed. 200 ml solution II were added, mixed by gentle shaking and incubated at room temperature for 30 minutes. 150 ml ice-cold solution III were then added and the mixture was incubated on ice for 5 minutes. The sample was centrifuged for 5 minutes at 13,000 rpm (MSE Microcentaur benchtop microfuge). The supernatant was extracted with an equal volume of phenol/chloroform and then IPA precipitated. The pellet was resuspended in 50 ml T10E1. RNA was digested by the addition of 1 ml 1 mg/ml RNaseA, followed by incubation at 37° C. for 30 minutes. Ten microlitres of this DNA were used in restriction enzyme digests and the identity of the binary plasmid was confirmed by agarose gel electrophoresis.

Transformation of Tobacco

Tobacco was transformed using the method developed by Horsch et al.(1985). The Agrobacterium containing the binary vector construct was grown in YEP broth, containing the appropriate antibiotics, at 30° C. for 24 hours prior to the transformation. The cells were pelleted by centrifugation at 3,000 rpm for 20 minutes at room temperature (Sorvall RC3C centrifuge, H6000A rotor) and resuspended in 10 mls fresh YEP. Leaf discs were cut from leaves of *Nicotiana tabacum* var. Samsun using a cork-borer (7 mm) and transferred to a 14 cm petri dish. The Agrobacterium was added to the petri dish which was left at room temperature for 30 minutes. Feeder plates were prepared before starting the experiment. One 1 NBM media (4.6 g MS salts [Flow Laboratories], 30 g sucrose, 0.1 mg EtOH NAA [Sigma], 0.1 mg BAP [Sigma], 8 g agar [Difco], 100X B5 VITS, pH 5.9) was required for 40 plates. One ml of a tobacco cell suspension culture was spread evenly over the surface of the plates, and then covered with a sterile 9 cm Whatman No. 1 filter disc. The leaf discs were transferred to the feeder plates, lower epidermis uppermost. After 2 days co-cultivation with the Agrobacterium the discs were transferred to NMB plates containing 100 µg/ml kanamycin sulphate and 500 µg/ml carbenicillin sodium salt, in order to eliminate the Agrobacterium and select for transformants. The leaf discs were transferred every 2 weeks to fresh NMB plates containing the antibiotics. After approximately 4 weeks small shoots were visible on the leaf discs. These were transferred to MS medium (4.6 g MS salts, 30 g sucrose, 8 g agar, pH 5.9) containing 200 µg/ml carbenicillin sodium salt and 100 µg/ml kanamycin sulphate. Transformants rooted after approximately 14 days while untransformed plants bleached and died. When the transformed plants were established they were transferred to soil and grown in the greenhouse.

Other modifications of the present invention will be apparent to those skilled in the art without departing from the scope of the invention.

References

Hatzios K K: An overview of the mechanisms of action herbicide safeners. Z Naturforsch 46c: 819–827 (1991).

Holt D C, Lay V, Clarke ED, Dinsmore A, Jepson I, Bright S W J, Greenland A J: Characterisation of the safener-induced glutathione S-transferase isoform II from maize. Planta (1995)196:295–302.

Irzyk G P, Fuerst E P: Purification and characterization of a glutathione S-transferase from benoxacor-treated maize (*Zea mays*). Plant Physiol 102: 803–810 (1993).

Jepson I, Bray J, Jenkins G, Schuch W, Edwards K: A rapid procedure for the construction of PCR cDNA libraries from small amounts of plant tissue. Plant Mol Biol Rep 9 (2): 131–138 (1991).

Lamoureux G L, Rusness D G: The role of glutathione and glutathione S-transferases in pesticide metabolism, selectivity, and mode of action in plants and insects. In Dolphin D, Poulson R, Avramovic O (eds), Coenzymes and cofactors, Vol 3: Glutathione: chemical, biochemical and medical aspects, part B pp 153–196. John Wiley and sons, New York (1989).

Mannervik B, Danielson U H: Glutathione transferases—structure and catalytic activity. Crit Rev Biochem 21: 283–337 (1988).

Mozer T J, Tiemeier D C, Jaworski E G: Purification and characterization of corn glutathione S-transferase. Biochemistry 22: 1068–1072 (1983).

Moore R E, Davies M S, O'Connell K M, Harding E I, Wiegand R C, Tiemeier D C: Cloning and expression of cDNA encoding a maize glutathione S-transferase in *E.coli*. Nucl Acids Res 14: 7227–7235 (1986).

Sanger F, Milkin S, Coulson AR: DNA sequencing with chain-terminating inhibitors. Proc Natl Acad Sci USA 74: 5463–5467 (1977).

Timmerman K P: Molecular characterization of corn glutathione S-transferase isozymes involved in herbicide detoxication: Physiologia Plantarum 77: 465471 (1989).

Wiegand R C, Shah D M, Mozer T J, Harding E 1, Diaz-Collier J, Saundres C, Jaworski E G, Tiemeier D C: Messenger RNA encoding a glutathione S-transferase responsible for herbicide tolerance in maize is induced in response to safener treatment: Plant Mol Biol 7: 235–243 (1986).

Kuhlemeier et al Ann Rev Plant Physiol. 38 221–257 (1987)

Drews, G. N., Beals, T. P., Bui, A. Q., and Goldberg, R. B. (1992). Regional and cell specific expresion patterns during petal development. Plant Cell 1383–1404.

Guerrero, Felix D., Crossland, Lyle., Smutzer, Gregory S., Hamilton, Douglas A., and Mascarenhas, Joseph P. (1990). Promoter sequences from a maize pollen-specific transcription in tobacco. Mol Gen Genet (1990) 224: 161–168.

Fonne-Pfister, Raymonde., and Kreuz, Klaus. (1990). Ring-methyl hydroxylation of chiortoluron by an inducible cytochrome P450-dependent enzyme from maize. Phytochemistry, Vol. 29, No. 9, pp. 2793–2796, 1990.

Schena, Mark., Lloyd, Alan M., and Davis, Ronald W. (1991). A steriod-inducible gene expression system for plant cells. Proc. Natl. Acad. Sci. USA. Vol. 88. pp. 10421–10425, December 1991. Genetics.

Williams, Shericca., Friedrich, Leslie., Dincher, Sandra., Carozzi, Nadine., Kessmann, Helmut., Ward, Eric., and Ryals, John. (1992). Chemical regulation of bacillus thuringiensis a-endotoxin expression in transgenic plants. Bio/Technology Vol. 10. May 1992.

Mett, Vadim L., Lochhead, Lessa P., and Reynolds, Paul H. S. (1993). Copper-controllable gene expression system for whole plants. Proc. Natt. Acad. Sci. USA. Vol. 90, pp. 45674571, May 1993. Plant Biology.

Weinmann, Pamela., Gossen, Manfred., Hillen, Wolfgang., Bujard, Hermann., and Gatz, Chrisiane. (1994). A chimeric transactivator allows tetracycline-responsive gene expression in whole plants. The Plant Journal (1994) 5 (4), 559–569.

Jefferson, R. A., Bevan, M., and Kavanagh, T. The use of the *Escherichia coli* beta-glucuronidase gene as a gene fusion marker for studies of gene expression in higher plants—construction of promoter cloning vector plasmid ptaki and detection of enzyme activity by fluorometric assay (conference paper). 060617 DBA Accession No: 87–04965.

Horsch, R. B. et al. (1985). A simple and general method for transferring genes into plants. Science 227:1229–1231.

Spychalla, J. P. and Bevan, M. W.(1993). Agrobacterium-mediated transformation of potato stem and tuber tissue, regeneration and PCR screening for transformation. Plant Tissue Culture Manual. B11:1–18.

We claim:

1. An isolated chemically inducible gene promoter sequence having a sequence of the region 1 to 897 base pairs immediately upstream of the transcription start point of the gene promoter sequence of the 27kD subunit of glutathione S-transferase.

2. An isolated chemically inducible gene promoter sequence having the sequence of the region 1 to 760 base pairs immediately upstream of the transcription start point of the gene promoter sequence of the 27kD subunit of glutathione S-transferase.

3. An isolated chemically inducible gene promoter sequence having the sequence of the region 1 to 570 base pairs immediately upstream of the transcription start point of the gene promoter sequence of the 27kD subunit of glutathione S-transferase.

4. An isolated chemically inducible gene promoter sequence having the sequence of the on 1 to 378 base pairs immediately upstream of the transcription start point of the gene promoter sequence of the 27kD subunit of glutathione S-transferase.

5. An isolated chemically inducible gene promoter sequence having the sequence of the region 267 to 332 base pairs immediately upstream of the transcription start point of the gene promoter sequence of the 27kD subunit of glutathione S-transferase.

6. An isolated chemically inducible gene promoter sequence having the sequence of the region 275 to 290 base pairs immediately upstream of the transcription start point of the gene promoter sequence of the 27kD subunit of glutathione S-transferase.

7. An isolated chemically inducible gene promoter element having the sequence of the region 267 to 279 base pairs immediately upstream of the transcription start point of the gene promoter sequence of the 27kD subunit of glutathione S-transferase.

8. An isolated chemically inducible gene promoter element having the sequence of the region 278 to 288 base pairs immediately upstream of the transcription start point of the gene promoter sequence of the 27kD subunit of glutathione S-transferase.

9. An isolated chemically inducible gene promoter element having the sequence of the region 286 to 296 base pairs immediately upstream of the transcription start point of the gene promoter sequence of the 27kD subunit of glutathione S-transferase.

10. An isolated chemically inducible gene promoter element having the sequence of the region 320 to 332 base pairs immediately upstream of the transcription start point of the gene promoter sequence of the 27kD subunit of glutathione S-transferase.

11. An isolated chemically inducible gene promoter sequence or element according to any one of claims 1–10 wherein the sequence or element is immediately upstream of the transcription start point of the gene promoter sequence of the 27kD subunit of maize glutathione S-transferase.

12. An isolated chemically inducible gene promoter sequence or element according to any one of claims 1–10 wherein the gene promoter sequence of the 27kD subunit of glutathione S-transferase, isoform II, is as shown in FIG. 1.

13. An isolated DNA molecule consisting of one or more of the sequences or elements of any one of claims 1 to 10.

14. A multimer of the sequences or elements of any one of claims 8 to 10.

15. A gene construct comprising a sequence or element of any one of claims 1 to 10 operatively linked to a gene or series of genes whereby expression of the gene or the series of genes is controlled by application of an effective exogenous inducer.

16. A plant having a construct as claimed in claim 10 integrated, preferably stably integrated within its genomic DNA by transformation.

17. A promoter/inducer combination wherein the promoter is the chemically inducible gene promoter sequence as claimed in any one of claims 1 to 6 or the chemically inducible promoter element of any one of claims 7 to 10.

18. An expression system for a plant, the expression system comprising a gene or a series of genes fused to a sequence or element as claimed in any one of claims 1 to 10 wherein the expression system is expressed in the plant and wherein expression of the gene or series of genes is controlled by application of an effective exogenous inducer.

19. An expression system for a plant comprising a construct according to claim 15, wherein the expression system is expressed in the plant and wherein expression of the gene or series of genes is controlled by application of an effective exogenous inducer.

20. A transgenic plant comprising an expression system according to claim 18 wherein the expression system is integrated, preferably stably integrated, within the plant's genomic DNA.

21. A method for inducing expression of a gene or a series of genes in a plant comprising the fusion of a sequence or element as claimed in any one of claims 1 to 10 to said gene or said series of genes, whereby expression of the gene or the series of genes is controlled by application of an effective exogenous inducer.

22. A process of expressing in a plant, a construct according to claim 15 wherein the construct is integrated, preferably stably integrated, within the plant's genomic DNA and whereby expression of the gene or series of genes is controlled by application of an effective exogenous inducer.

23. A multimer of the sequences or elements of claim 11.

24. A multimer of the sequences or elements of claim 12.

25. A process of expressing in a plant, an expression system according to claim 19 wherein the expression system is integrated, preferably stably integrated, within the plant's genomic DNA and whereby expression of the gene or series of genes may be controlled by application of an effective exogenous inducer.

* * * * *